US009314485B2

(12) United States Patent
Merkenschlager

(10) Patent No.: US 9,314,485 B2
(45) Date of Patent: Apr. 19, 2016

(54) USE OF PI3K M-TOR AND AKT INHIBITORS TO INDUCE FOXP3 EXPRESSION AND GENERATE REGULATORY T CELLS

(71) Applicant: Medical Research Council, Swindon (GB)

(72) Inventor: Matthias Michael Merkenschlager, London (GB)

(73) Assignee: MEDICAL RESEARCH COUNCIL, Swindon (GB)

( * ) Notice: Subject to any disclaimer, the term of this patent is extended or adjusted under 35 U.S.C. 154(b) by 0 days.

(21) Appl. No.: 14/527,044

(22) Filed: Oct. 29, 2014

(65) Prior Publication Data

US 2015/0147304 A1    May 28, 2015

Related U.S. Application Data

(63) Continuation of application No. 12/518,739, filed as application No. PCT/GB2007/004784 on Dec. 13, 2007, now abandoned.

(60) Provisional application No. 60/874,683, filed on Dec. 14, 2006, provisional application No. 60/912,448, filed on Apr. 18, 2007.

(30) Foreign Application Priority Data

Dec. 14, 2006  (GB) .................................. 0624999.9
Apr. 19, 2007  (GB) .................................. 0707609.4

(51) Int. Cl.
*A61K 35/17*      (2015.01)
*C12N 5/0783*    (2010.01)
*A61K 35/12*      (2015.01)

(52) U.S. Cl.
CPC .............. *A61K 35/17* (2013.01); *C12N 5/0636* (2013.01); *C12N 5/0637* (2013.01); *A61K 2035/122* (2013.01); *C12N 2501/40* (2013.01); *C12N 2501/51* (2013.01); *C12N 2501/515* (2013.01); *C12N 2501/60* (2013.01); *C12N 2501/70* (2013.01); *C12N 2501/999* (2013.01); *C12N 2506/11* (2013.01)

(58) Field of Classification Search
CPC ...................................................... A61K 35/17
See application file for complete search history.

(56) References Cited

U.S. PATENT DOCUMENTS

2004/0072766 A1   4/2004   June
2004/0126781 A1   7/2004   Ling et al.
2005/0261317 A1   11/2005  Sadhu et al.

FOREIGN PATENT DOCUMENTS

WO    2004/032867    4/2004

OTHER PUBLICATIONS

Battaglia et al., "Rapamycin selectively expands CD4+CD25+FoxP3+ regulatory T cells," Blood Journal, 105:4743-4748 (2005).
Chen et al., "Conversation of Peripheral CD4+CD25- Naive T Cells to CD4+CD25+ Regulatory T Cells by Tgf-β Induction of Transcription Factor Foxp3,"The Journal of Experimental Medicine, 198(12):1875-1886 (2003).
Cobb et al., "T cell lineage choice and differentiation in the absence of the RNase III enzyme Dicer," The Journal of Experimental Medicine, 201(9):1367-1373 (2005).
Foey et al., "Cytokine-simulated T cells induce macrophage IL-10 production dependent on phosphatidylinositol 3-kinase and p70S6K: implications for rheumatoid arthritis," Arthritis Research, 4(1):64-70 (2002).
Inman et al., "SB-431542 Is a Potent and Specific Inhibitor of Transforming Growth Factor-α Superfamily Type I Activin Receptor-Like Kinase (ALK) Receptors ALK4, ALK5, and ALK7," Molecular Pharmacology, 62(1):65-74 (2002).
Camps et al., Blockade of PI3Kγ suppresses joint inflammation and damage in mouse models of rheumatoid arthritis, Nature Medicine, 11(9):936-943 (2005).
Davies et al., "Specificity and mechanism of action of some commonly used protein kinase inhibitors," Biochem. J. 351:95-105 (2000).
Knight et al., "A Pharmacological Map of the PI3-K Family Defines a Role for p110α in Insulin Signaling," Cell, 125:733-747 (2006).
Kretchmer et al., "Inducing and expanding regulatory T Cell populations by foreign antigen," Nature Immunology, 6(12):1219-1227 (2005).
Thompson et al., "Ikaros DNA-Binding Proteins as Integral Components of B Cell Development-Stage-Specific Regulatory Circuits," Immunity, 26:335-344 (2007).
Zheng et al., Favorably Tipping the Balance between Cytopathic and Regulatory T Cells to Create Transplantation Tolerance, Immunity, 19:503-514 (2003).
Keever-Taylor et al., "Rapamycin Added to Human CD25+ Cell Cultures Activated Through CD3/CD28 Enriches for CD4+CD25+CD27+Foxp+ Regulatory T Cells," Biol. Blood Bone Marrow Transpl., 12(S1):14 (2006).
Ward et al., "Therapeutic Potential of Phosphoinositide 3-Kinase Inhibitors," Chemistry & Biology, 144:207-213 (2003).
Breslin et al., "LY294002 and rapamycin co-operate to inhibit T-cell proliferation," British Journal of Pharmacology, 144(6):791-800 (2005).
Bensinger et al., "Distinct IL-2 Receptor Signaling Pattern in CD4+CD25+ Regulatory T Cells," The Journal of Immunology, 172:5287-5296 (2004).

*Primary Examiner* — Amber D Steele
(74) *Attorney, Agent, or Firm* — McAndrews, Held & Malloy Ltd.

(57) ABSTRACT

The invention relates to a method of inducing Foxp3 expression in a T cell comprising
 (i) stimulating a T cell
 (ii) inhibiting signalling via PI3K alpha or PI3K delta or m-TOR or Akt in said T cell, wherein said inhibition is commenced 10 to 22 hours after the stimulation of (i). The invention also relates to certain uses of PI3K inhibitors, PI3K inhibitors for particular uses, and kits.

19 Claims, 14 Drawing Sheets

Figure 1. TCR signal deprivation induces Foxp3 expression by newly activated T cells in synergy with inhibitors of the PI3-K/mTOR pathway
a 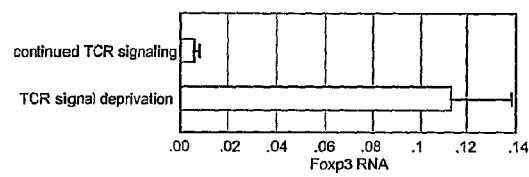
b 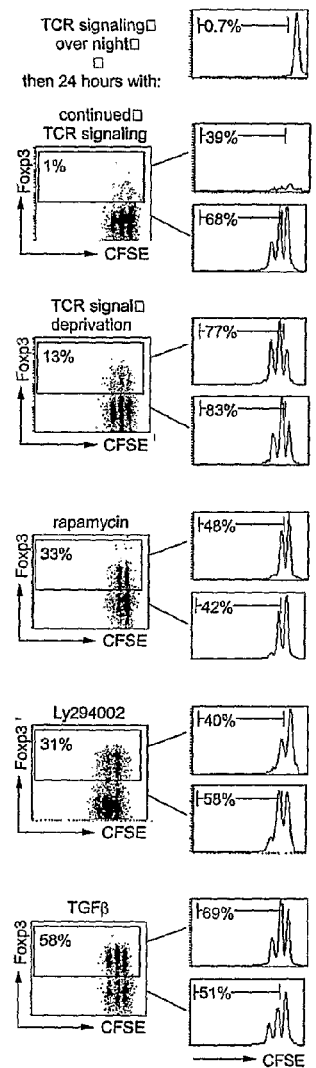

C

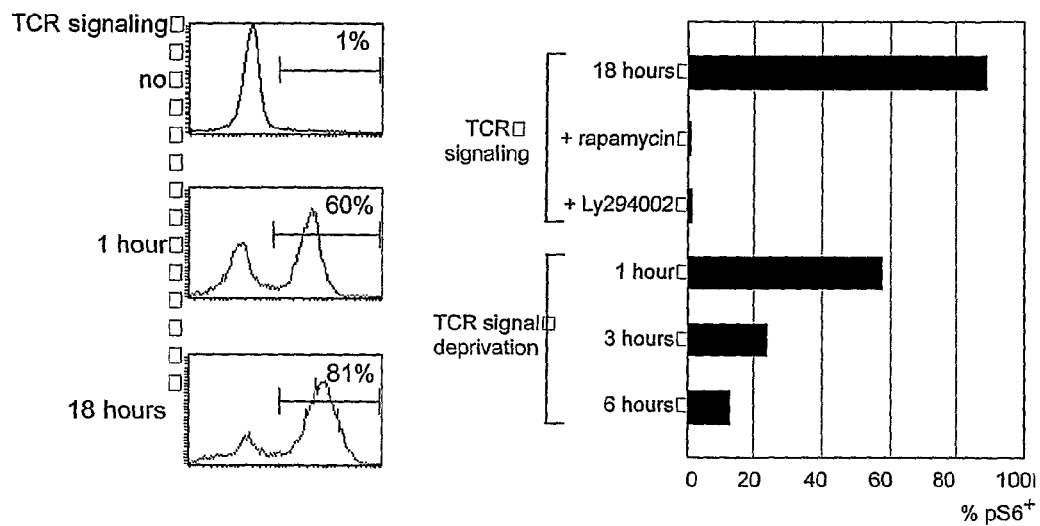
Figure 2. TCR signaling controls mTOR activity in newly activated CD4 T cells

Figure 3. Induction of Foxp3 by TCR signal deprivation and PI3K/mTOR inhibitors is stable and results in the acquisition of regulatory function.
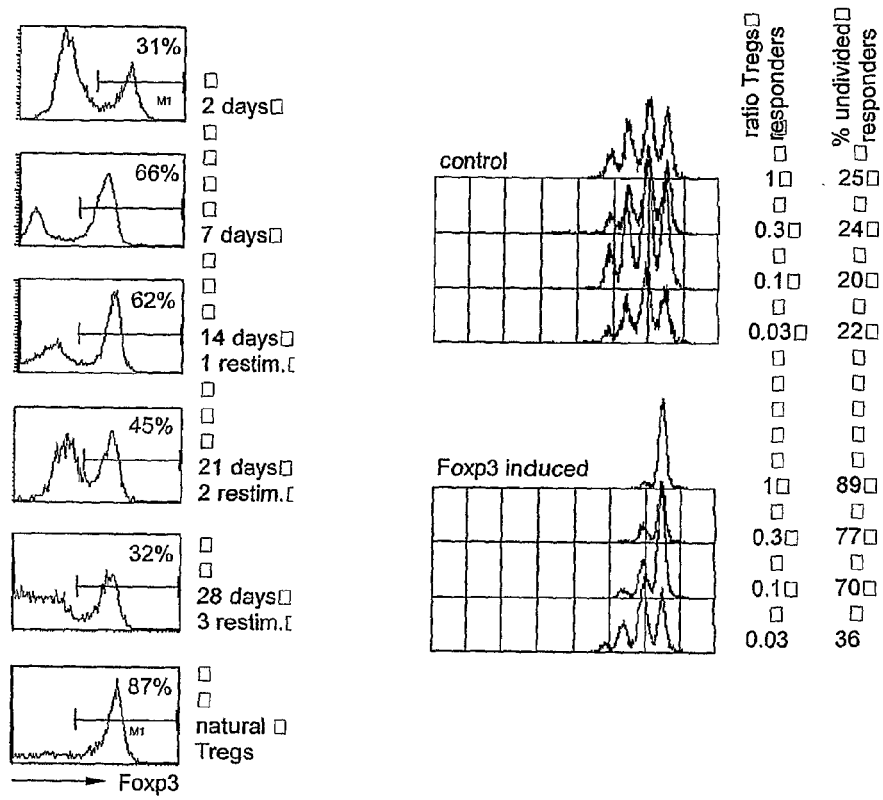
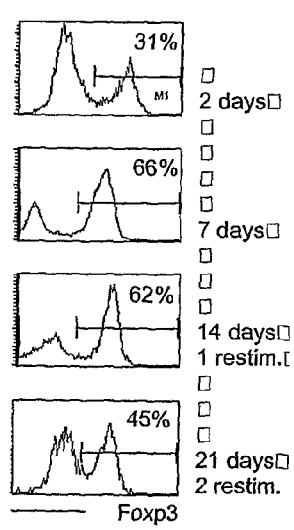

Figure 4. Foxp3 expression in response to TCR signal deprivation and PI3-K/mTOR inhibition in vivo
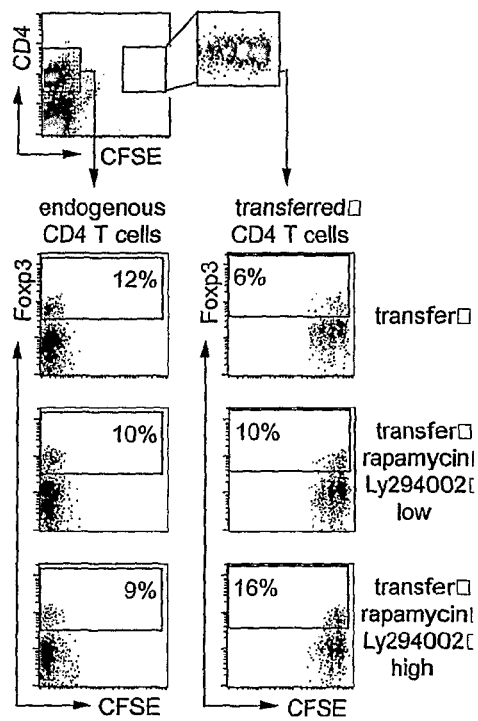
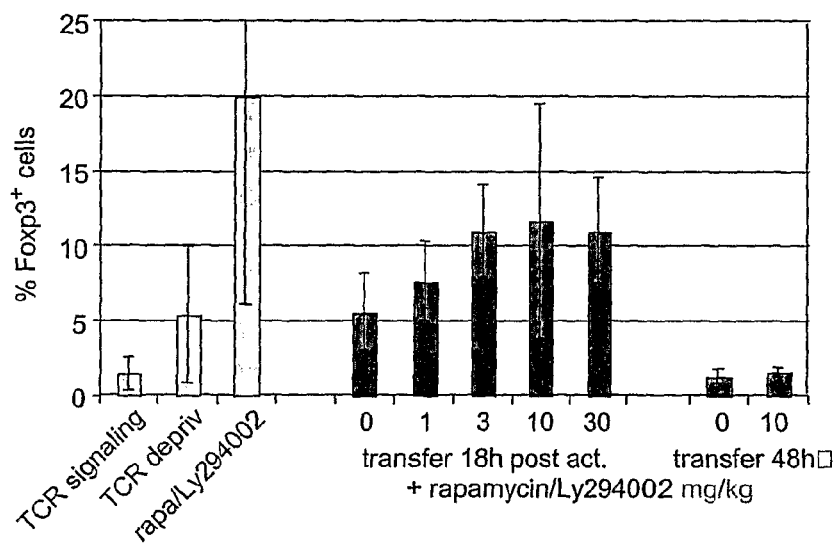

Figure 5. Differential involvement of p110 isoenzymes in Foxp3 induction
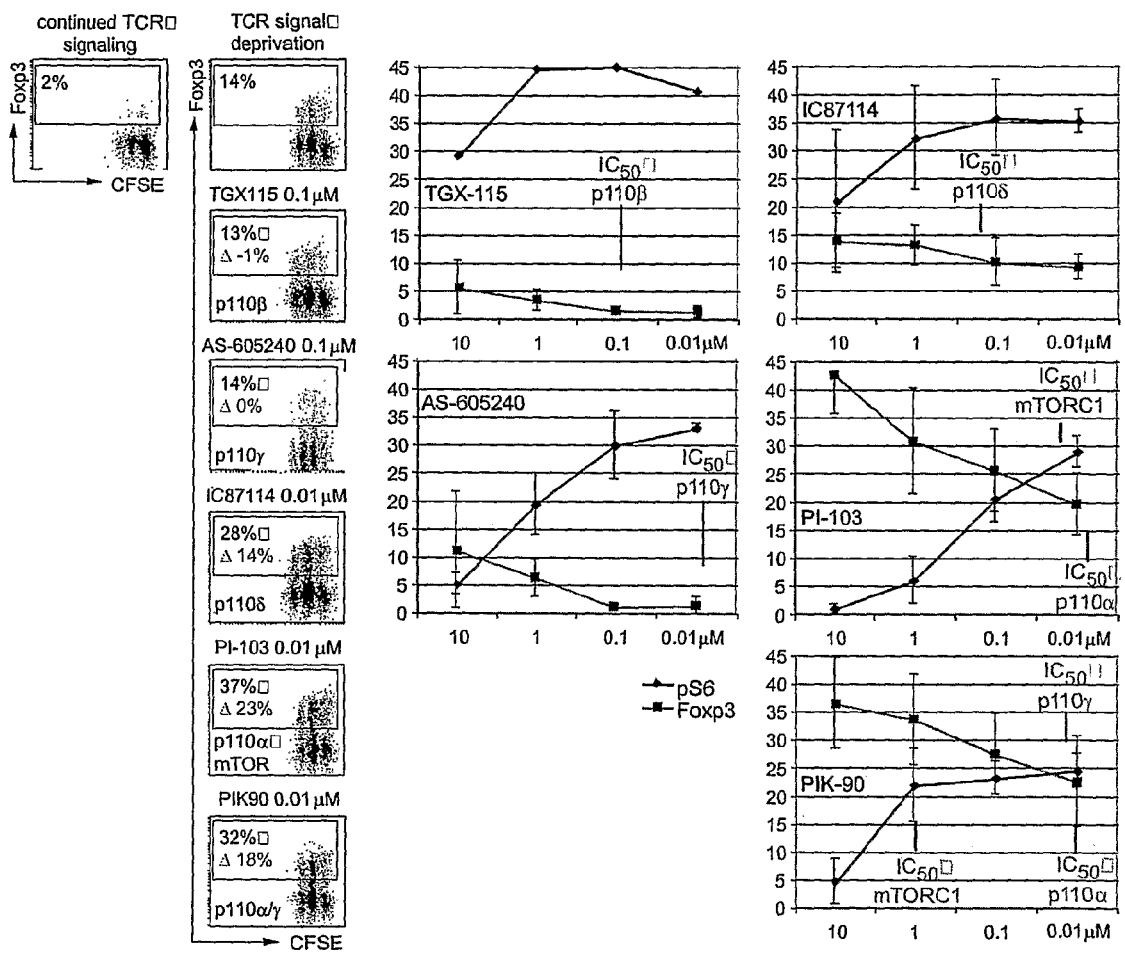

Figure 6. Foxp3 induction by inhibitors of PI3K/mTOR signaling is independent of TGFβ.
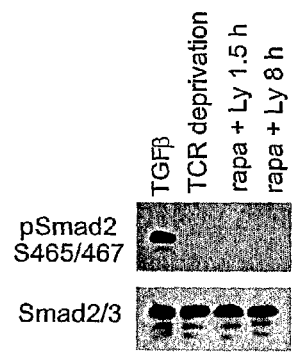
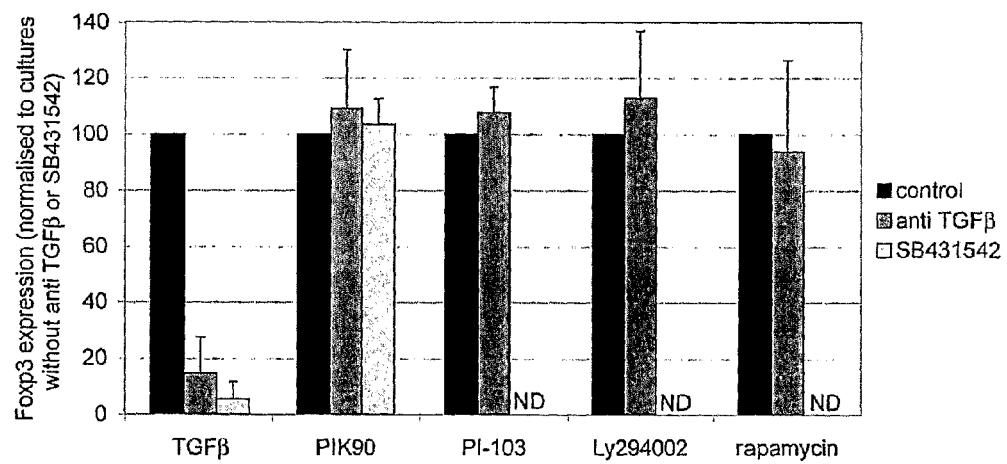

USE OF PI3K M-TOR AND AKT INHIBITORS TO INDUCE FOXP3 EXPRESSION AND GENERATE REGULATORY T CELLS

The present application is filed as a continuation of U.S. patent application Ser. No. 12/518,739, which was filed Dec. 13, 2007, which was filed pursuant to 35 U.S.C. 371 as a U.S. National Phase application of International Patent Application No. PCT/GB07/04784, which was filed Dec. 13, 2007, claiming the benefit of priority to British Patent Application No. 0624999.9, which was filed on Dec. 14, 2006, U.S. Provisional Patent Application No. 60/874,683, which was filed on Dec. 14, 2006, U.S. Provisional Patent Application No. 60/912,448, which was filed on Apr. 18, 2007, and British Patent Application No. 07078609.4, which was filed on Apr. 19, 2007. The entire text of the aforementioned applications is incorporated herein by reference in its entirety.

FIELD OF THE INVENTION

The invention relates to new uses of phosphatidyl inositol-3-kinase (PI3K) inhibitors. In particular, the invention relates to new methods for induction of Foxp3 expression in T cells.

This application contains a sequence listing "20823US01_SeqList.txt" that was created on Jul. 31, 2012 and 1,437 bytes in size. The sequence listing is submitted in electronic form only and is incorporated herein by reference.

BACKGROUND TO THE INVENTION

Regulatory T cells (Treg cells) are essential for preventing autoimmunity and immune pathology, which are caused by effector T cells in the absence of Treg cells Immune interventions aimed at restraining effector T cells (to limit autoimmunity and immune pathology) or boosting immune responses (e.g. against tumours) require approaches that change the balance between Treg cells and effector T cells. Current approaches are slow, inefficient, rely on the use of bioactive peptides purified from biological sources, or on the expansion of pre-existing Treg cells.

Expression of the transcriptional regulator Foxp3, an intracellular protein and member of the forkhead/winged-helix family of transcriptional regulators, is characteristic of Treg cells.

Treatment of T cells with the bioactive peptide TGFbeta is known to induce de novo expression of Foxp3 (Chen et al., 2003 J. Exp. Med. vol 198, pp 1875-1886).

Certain in vivo immunisation protocols have been reported to induce Foxp3 expression in T cell receptor transgenic T cells (Kretschmer et al., 2005 Nature Immunol. vol 6 p 1219). This approach requires knowledge of both the specificity for antigen and the MHC restriction of the target T cells, so that the antigen used for immunisation can be selected accordingly. This condition is met by artificial experimental systems in which T cells carry transgenic T cell receptors. It is a problem with this approach that this condition is not met for naturally occurring autoimmune diseases.

The mTOR inhibitor rapamycin (sirolimus) has been used to manipulate the expansion of pre-existing Treg cells expressing Foxp3 (Zheng et al., 2003 Immunity vol 19 p 503; Battaglia et al., 2005 Blood vol 105 p 4743). However, such treatments have been shown not to induce the de novo expression of Foxp3, which is a problem. For example, Battaglia et al (ibid) states 'The presence of CD4 CD25 Tr cells . . . in rapamycin-exposed T-cell cultures may be due to either a de novo induction of CD25 Tr cells from CD25 T cells or to a selective expansion of the naturally occurring CD4 CD25 FoxP3 Tr-cell subset already present in limited amounts at the beginning of the culture (ie, the 10% of CD4 CD25bright T cells usually found in a naive spleen). To address this question, CD4 T cells depleted of the CD25 Tr cells were cultured for 3 weeks in the presence or absence of rapamycin. In contrast to CD4 T cells (FIG. 3A), CD4 CD25 T cells activated in the presence of rapamycin gave rise to a population of T cells that failed to suppress cell proliferation in vitro (FIG. 4A). Accordingly, FoxP3 expression was enhanced in CD4 T cells exposed to rapamycin but not in CD4 CD25 rapamycin-treated T cells (FIG. 4B)'. Furthermore, the protocols employed rely on multiple rounds of in vitro stimulation over several weeks, which has the drawback of being very labour intensive. Negative effects of rapamycin on Treg cell numbers have also been reported in the art. Rapamycin is not a synthetic compound and can therefore suffer from problems of impurities and/or variation or formulation problems.

Thus, prior art techniques are typically operating via stimulation or activation of existing Tregs which can enhance Foxp3 expression in cells already expressing it, or are based on blocking non-Tregs, leading to expansion/selection or over-representation of Tregs in the population. These outcomes are the same as rapamycin treatment as noted above. Another example is the use of TGFbeta which typically enhances an already present level of Foxp3 expression. No such approaches lead to de novo Foxp3 expression/de novo Tregs.

Gene targeting of the PI3K isoenzyme p110delta results in increased Treg cell numbers in the thymus, but in decreased Treg cell numbers in peripheral lymphoid organs. This is accompanied by inflammatory bowel disease, which is often linked to Treg cell deficiencies. No clear conclusions about a relationship between PI3K signalling and Foxp3 expression can be drawn from these studies.

Inhibitors of the PI3K isoenzyme p110gamma are under evaluation for the treatment of autoimmune diseases based on mechanisms distinct from Treg cells.

WO2004/032867A3 discloses molecules preferentially associated with effector T cells or regulatory T cells and methods of their use. This document presents population level studies. PI3K inhibitors are mentioned on page 76 of this document and in FIG. 23A. The effects on Foxp3 expression (if any—high doses of inhibitor according to this document are probably cytotoxic and the low doses arguably show no significant effect) appear to be due to an expansion of Foxp3 expressing cells, or an enhancement in expression of Foxp3 in Foxp3 expressing cells. There is no evidence of de novo Foxp3 expression in the teachings of WO2004/032867A3. The underlying principle of this document is in attempting to tilt the balance of the immune system, for example to try to generally reduce autoimmunity or to try to generally enhance responses. There is no teaching of, and no suggestion towards, making new Tregs. Their method at best teaches that resting cells (PBL) are simultaneously activated (CD3/CD28) and inhibited (LY294002), i.e. activation and stimulation at the same time. In common with other prior art studies (e.g. Battaglia (ibid.)), and in common with the inventors' own studies, such treatments do not generate de novo Foxp3 expression/de novo Tregs.

US2004/0072766 discloses methods for modulating T cell responses by manipulating intracellular signal transduction. The methods disclosed in this document involve the addition of stimulators and inhibitors together i.e. at once or simultaneously. No de novo Foxp3 expression is generated in this approach.

Foey et al (Arthritis Res 2002 vol 4 pp 64-70) disclose that cytokine stimulated T cells induce macrophage IL-10 production dependent on phosphatidyl inositol 3-kinase and p70S6K and the implications for rheumatoid arthritis. This relates to the study of macrophages in the presence of T cells. The T cells were fixed to separate the effects before and after contact. Thus, the cells are fixed and no longer alive when the PI3K inhibitors are added in these methods. Thus no de novo Foxp3 expression is produced by these methods.

Breslin et al disclose that rapamycin and LY294002 co-operate to inhibit T cell proliferation. This example, in common with other studies, involves exposing T cells to inhibitors in order to study aspects of their biology such as proliferation. The inhibitors are added before stimulation, typically at least 30 minutes prior to stimulation. Cell numbers or other parameters are then examined. No de novo Foxp3 expression is generated by such techniques.

US2005/0261317 disclose inhibitors of human PI3K delta. This document merely examines certain neutrophils, B cells and certain exocytotic cells, and is not connected with T cells or Tregs. The data presented are merely aimed at validating that the PI3K inhibitors disclosed actually block the relevant functions.

US2004/0126781 discloses methods of preventing immune-mediated abortion by inhibiting a CD28-mediated costimulatory signal. These methods involve blocking of CD28 with soluble ligand. Blocking of CD28 with soluble ligand is clearly mutually exclusive with stimulation/activation of T cells.

The present invention seeks to overcome problem(s) associated with the prior art.

SUMMARY OF THE INVENTION

Foxp3 expression has been associated with regulatory T cell function. In certain settings, Foxp3 expression has been shown to be necessary and sufficient to induce regulatory T cell function. Indeed, Foxp3 expression has in some circumstances been regarded as an indicator or identifier of regulatory T cells as compared to other sub-populations of T cells. In the prior art, the only known way of inducing Foxp3 expression pharmacologically has been by treating a population of T cells with the bioactive peptide TGFβ.

The present inventors have surprisingly discovered a new technique for induction of Foxp3 expression. This new method involves the use of PI3-K inhibitors which have not previously been shown to induce Foxp3 expression.

A key finding of the present inventors is with regard to the timing of treatments to the target cells. Specifically the inventors have found that the inhibitors (such as PI3K inhibitors) must be added to the cells only after they have been stimulated. Thus the stimulation/activation step must be followed by incubation or a time delay before inhibitors are contacted with the cells. Addition of inhibitors simultaneously with or even before activation does not lead to de novo Foxp3 expression. It is thus a key teaching of the invention that the inhibitors should be added after stimulation/activation. These important timings are discussed in more detail below.

Although certain PI3-K inhibitors have been shown to inhibit mTOR, there is no evidence of them acting to induce Foxp3 expression. Furthermore, although rapamycin (which acts on mTOR) has been shown to be able to selectively expand CD4+ CD25+ Foxp3+ regulatory T cells, there has been no demonstration of any induction of de novo Foxp3 expression using such a technique. Therefore, the discovery made by the present inventors that certain PI3-K inhibitors can directly lead to induction of de novo Foxp3 expression in T cells, and to Treg function, is a surprising and significant advance.

The present invention is based on these surprising findings.

Thus, in a first aspect the invention provides a method of inducing Foxp3 expression in a T cell comprising
(i) stimulating a T cell
(ii) inhibiting signalling via PI3K alpha or PI3K delta or m-TOR or Akt in said T cell, wherein said inhibition is commenced 10 to 22 hours after the stimulation of (i).

In another aspect, the invention relates to a method of inducing Foxp3 expression in a previously stimulated T cell comprising inhibiting signalling in said T cell via PI3K alpha or PI3K delta or m-TOR or Akt, wherein said inhibition is commenced 10 to 22 hours after the stimulation.

In another aspect, the invention relates to a method of treating a subject in need of regulatory T cell(s) comprising
(i) removing a sample comprising a T cell from a subject
(ii) stimulating said T cell
(iii) optionally withdrawing said stimulation
(iv) inhibiting signalling via PI3K alpha or PI3K delta or m-TOR or Akt in said T cell, wherein said inhibition is commenced 10 to 22 hours after the stimulation of (i); and
(v) reintroducing said T cell to said subject.

Suitably said inhibition is commenced about 17 to 19 hours after the stimulation.

Suitably said inhibition is commenced about 18 hours after the stimulation.

Suitably the inhibiting signalling step comprises inhibiting signalling via PI3K alpha or PI3K delta.

Suitably inhibiting signalling via PI3K alpha or PI3K delta comprises contacting said cell with PI3K inhibitor, and wherein said inhibitor inhibits PI3K alpha and/or PI3K delta.

Suitably said method(s) further comprise withdrawing said stimulation no later than at the time of inhibiting signalling.

In another aspect, the invention relates to a method for generating a regulatory T-cell comprising
(i) stimulating a T cell
(ii) inhibiting signalling via PI3K alpha or PI3K delta or m-TOR or Akt in said T cell, wherein said inhibition is commenced 10 to 22 hours after the stimulation of (i).

In another aspect, the invention relates to a method for generating a regulatory T-cell comprising treating a stimulated CD8− T cell with phosphatidyl inositol 3 kinase (PI3K) inhibitor wherein said inhibitor inhibits PI3K alpha and/or PI3K delta.

In another aspect, the invention relates to a method for generating a regulatory T-cell comprising treating a stimulated T cell with phosphatidyl inositol 3 kinase (PI3K) inhibitor wherein said inhibitor inhibits PI3K alpha and/or PI3K delta.

In another aspect, the invention provides a method for generating a regulatory T-cell comprising treating a stimulated T cell with m-TOR inhibitor. The m-TOR inhibitor may be any known m-TOR inhibitor such as rapamycin (sirolimus), or an analogue thereof such as RAD001 (everolimus), CCI-779 (temsirolimus), AP23573, or a combined m-TOR/p110alpha inhibitor such as PI103. Preferably said m-TOR inhibitor is rapamycin.

Stimulation may be by any suitable means which renders the T cell sensitive to the action of PI3K inhibitors and/or m-TOR inhibitors for Treg production as described herein. Preferably stimulation of the T cell is by stimulation of the TCR receptor. In some embodiments this stimulation may be a persistent or enduring stimulation, which means that the stimulation is not necessarily withdrawn at the time of action of PI3K and/or m-TOR inhibitors. Preferably a stimulated T cell is a T cell which has been stimulated via the T cell receptor. More preferably stimulation of the T cell is by stimulation of the TCR receptor followed by withdrawal of said TCR receptor stimulation. In another embodiment stimulation may be via CD3. In either case, preferably a costimulatory receptor such as CD28 is also stimulated. Preferably CD28 is stimulated at the same time as stimulation of the TCR or CD3 receptor(s). In a preferred embodiment stimulation is via simultaneous stimulation of TCR and/or CD3, and of CD28, preferably followed by withdrawal of stimulation via TCR and CD3. Withdrawal of stimulation may refer to the simple removal of signal, or may refer to more active methods such as blocking costimulation of CD3/CD28 at the time of addition of inhibitor(s).

Preferred embodiments of the invention may further comprise a signal deprivation step e.g. as set out in the examples section.

In another aspect, the invention provides a method for generating a regulatory T-cell comprising (i) stimulating a T cell; (ii) optionally withdrawing said stimulation; and (iii) inhibiting signalling via PI3K alpha or PI3K delta and/or via m-TOR and/or via Akt in said T cell. Preferably step (ii) comprises withdrawing said stimulation.

Stimulation of said T cell may be via stimulation of the TCR receptor or via CD3, and a costimulatory receptor such as CD28. Preferably stimulation is via the T cell receptor followed by withdrawal of said stimulation via the T cell receptor.

In another aspect, the invention provides a method of treating a subject in need of regulatory T cell(s) comprising
 (i) removing a sample comprising a T cell from a subject
 (ii) stimulating said T cell
 (iii) optionally withdrawing said stimulation
 (iv) inhibiting signalling in said T cell via PI3K alpha or PI3K delta and/or m-TOR and/or Akt; and
 (v) reintroducing said T cell to said subject. Preferably step (iii) comprises withdrawing said stimulation.

Preferably stimulating said T cell comprises contacting said T cell with anti-TCR or anti-CD3 antibody. Preferably stimulating said T cell further comprises contacting said T cell with anti-CD28 antibody, preferably contacting said T cell with anti-TCR or anti-CD3 antibody, and with anti-CD28 antibody simultaneously. The mode of presentation of such antibodies may be chosen by the operator, for example this may be accomplished using plate-bound antibodies or by using beads coated with antibodies such as anti-CD3/anti-CD28 antibodies, or by any other means of presentation known to the operator.

In another embodiment stimulation may be by contact of the target cells such as peripheral T cells with antigen presenting cells, such as antigen presenting cells contacted with specific peptide antigen. In these embodiments, as in embodiments involving other modes of stimulation, said stimulation may be enduring or persistent meaning that the stimulation is not withdrawn at the time of m-TOR/PI3K/Akt inhibition. In other embodiments the stimulation may be withdrawn at the time of m-TOR/PI3K/Akt inhibition, may be withdrawn before the time of m-TOR/PI3K/Akt inhibition, suitably the stimulation may be withdrawn at the time of m-TOR/PI3K/Akt inhibition.

In another aspect, the invention provides a method of inducing Foxp3 expression in a previously stimulated T cell comprising inhibiting signalling in said T cell via PI3K alpha or PI3K delta and/or m-TOR and/or Akt.

In another aspect, the invention provides a method of inducing Foxp3 expression in a T cell comprising stimulating a T cell; withdrawing said stimulation; and inhibiting signalling in said T cell via PI3K alpha or PI3K delta and/or m-TOR and/or Akt. Preferably said method comprises inducing Foxp3 expression in a T cell by stimulating a T cell via the T cell receptor; withdrawing said stimulation via the T cell receptor; and inhibiting signalling in said T cell via PI3K alpha or PI3K delta and/or m-TOR and/or Akt.

In another aspect, the invention provides a method as described above wherein inhibiting signalling via PI3K alpha or PI3K delta and/or m-TOR and/or Akt comprises inhibiting signalling via PI3K alpha or PI3K delta. Preferably inhibiting signalling via PI3K alpha or PI3K delta comprises contacting said cell with PI3K inhibitor. Preferably said inhibitor inhibits PI3K alpha and/or PI3K delta.

When inhibiting signalling via PI3K alpha or PI3K delta or m-TOR or Akt comprises inhibiting signalling via m-TOR, preferably inhibiting signalling via m-TOR comprises contacting said cell with rapamycin.

In another aspect, the invention provides use of a PI3K inhibitor in the induction of differentiation of a T cell into a regulatory T cell wherein said inhibitor inhibits PI3K alpha and/or PI3K delta.

In another aspect, the invention provides use of a PI3K inhibitor in the induction of Foxp3 expression wherein said inhibitor inhibits PI3K alpha and/or PI3K delta.

In another aspect, the invention provides use of a PI3K alpha inhibitor or a PI3K delta inhibitor for the manufacture of a medicament for deficiency of regulatory T cells.

Preferably the deficiency of regulatory T cells is an autoimmune disorder or an immune pathology. Preferably said deficiency is rheumatoid arthritis or diabetes, preferably type I diabetes, colitis, or a lymphoproliferative disorder where the presence of Treg cells indicates a favourable prognosis, preferably a B cell lymphoma.

In another aspect, the invention provides a PI3K alpha inhibitor for use in the treatment of a deficiency of regulatory T cells.

In another aspect, the invention provides a PI3K delta inhibitor for use in the treatment of a deficiency of regulatory T cells.

In another aspect, the invention provides a m-TOR inhibitor for use in the treatment of a deficiency of regulatory T cells.

In another aspect, the invention provides an Akt inhibitor for use in the treatment of a deficiency of regulatory T cells.

In another aspect, the invention provides a kit comprising a TCR stimulant and an inhibitor of PI3K alpha or delta and/or an inhibitor of m-TOR and/or an inhibitor of Akt.

In another aspect, the invention provides a kit as described above wherein said TCR stimulant comprises anti-TCR or anti-CD3, and anti-CD28. Preferably the anti-TCR/anti-CD3/anti-CD28 agents are antibodies to TCR/CD3/CD28 respectively.

In another aspect, the invention provides a kit as described above further comprising an m-TOR inhibitor such as rapamycin. A m-TOR inhibitor may be advantageously used in expansion of the Foxp3 expressing T cells generated by use of the TCR stimulant/PI3K inhibitor of the kits of the invention. Furthermore, a m-TOR inhibitor may advantageously increase the efficiency of Foxp3 induction.

In another aspect, the invention provides a kit as described above further comprising an Akt inhibitor.

In a most preferred embodiment, the inhibitor is a PI3K inhibitor. Preferably said PI3K inhibitor comprises LY294002; preferably said PI3K inhibitor comprises a class IA PI3K inhibitor such as PIK-90 (alpha/m-TOR), PI-103 (alpha/gamma) or YM-024 (alpha/delta).

Preferable Aspects

Suitably the starting population of cells (target cells) in which Foxp3 is to be induced are depleted of pre-existing Tregs. Suitably the starting population of cells is depleted of CD25+ cells. If a population of cells comprises less than 1% Tregs we consider it to be depleted of Tregs or effectively free of Tregs. Suitably the starting population of cells does not comprise Tregs. Suitably the method of the invention comprises a further step of such depletion; suitably such step is carried out before stimulation.

Suitably the starting population of cells (target cells) in which Foxp3 is to be induced are enriched for naïve T cells. Suitably the starting population is enriched for CD62L cells and/or enriched for CD45Rb cells. Suitably the starting population is enriched for CD62L cells and enriched for CD45Rb cells. Suitably the method of the invention comprises a further step of such enrichment; suitably such step is carried out before stimulation.

It is a key feature of the invention that activation and inhibition of the cells are chronologically separated. Simultaneous activation and inhibition does not lead to de novo Foxp3 expression. Suitably activation and inhibition are not performed simultaneously according to the present invention. This has happened in the prior art and does not lead to de novo Foxp3 expression. For example, with reference to FIG. 1C herein, the '0' timepoint is indicative of prior art treatments— this represents 0 hours between stimulation/activation and addition of inhibitors i.e. inhibitors added at the same time as activation/stimulation. It is very clear that this treatment is ineffective at induction of de novo Foxp3 expression. By contrast, treatments according to the present invention involving a delay or incubation between stimulation and inhibition are effective for induction of de novo Foxp3 expression. This does not mean that inhibitors cannot be added with activators still present, but means that activation must precede inhibition or that inhibition must occur after activation. The time of separation can be very important and is a key contribution to the art. The time between activation and inhibition may be specifically chosen for particular application(s) as taught herein. Exemplary timings are when inhibitor treatment is applied approx. 12-18 hours after activation, suitably about 18 hours after activation. This is discussed in more detail below.

Suitably the methods of the invention are applied to induce Foxp3 without a requirement for expansion of the cells.

It is an advantage of the invention that cells of a desired specificity may be converted to Tregs. It is this capability which provides a number of the advantages set out herein.

DETAILED DESCRIPTION OF THE INVENTION

Specialised cell types in multicellular organisms are defined by specific patterns of gene expression. During their differentiation from hematopoietic stem cells, naive CD4 T cells have undergone considerable restriction of their developmental potential, but a number of options remain open to them, namely Th1, Th2, Th17, and Treg. The choice of Th lineage is important for effective immune responses to specific pathogens, while the balance between effector and regulatory functions is critical to ensure immune competence while avoiding excessive immune pathology and autoimmunity. Natural regulatory T cells are characterised by the expression of the signature transcription factor Foxp3 and persistent expression of Foxp3 is both necessary and sufficient for regulatory T cell function. Tregs arise 'naturally' in the thymus and can arise from naive peripheral CD4 T cells. We identify signals that induce Foxp3 expression and regulatory T cell function in naive CD4 T cells. We disclose that Foxp3 expression is induced when newly activated T cells are deprived of TCR signals. In this setting, Foxp3 induction is selectively potentiated by inhibitors of the PI3K/mTOR axis and appears to be independent of TGFbeta, the classical inducer of Treg differentiation.

In particular the invention provides use of PI3-K/mTOR inhibitors, preferably PI3K inhibitors, which synergise with TCR signal deprivation to induce Foxp3 in newly activated CD4 T cells.

Activation of naive CD4 T cells reveals their potential to become effector or regulatory T cells (Tregs). While effectors mediate immune responses, Tregs balance effector T cells, maintain homeostasis and prevent immune pathology. We describe novel methods for the stable induction of Foxp3, the signature transcription factor of Tregs, which is initiated when newly activated T cells are deprived of TCR signals, and potentiated by inhibitors of PI3K/mTOR, preferably small molecule inhibitors of PI3K. Selective inhibition of class I PI3K catalytic subunits identifies p110alpha and p110delta— but not p110gamma or p110beta—as regulators of Foxp3. Foxp3 induction is independent of exogenous TGFbeta and resistant to neutralising TGFbeta antibodies and pharmacological antagonists of Smad signaling. These disclosures enable new approaches to manipulate regulatory T cell differentiation.

It is to be noted that it is an advantage of the present invention that de novo Foxp3 expression is being induced. This is contrasted with the situation in the prior art where the best effect shown to date has been the expansion of T cells which are already expressing Foxp3. The opportunity to actively induce Foxp3 expression in cells which are not currently expressing it is a significant advantage of the present invention.

We show that small molecule inhibitors of the PI3K/mTOR pathway rapidly and efficiently induce the de novo expression of Foxp3, the signature transcription factor of the Treg cell lineage. This enables new therapeutic approaches to be applied to clinical settings where the de novo generation of Treg cells is desirable, such as the prevention and the treatment of autoimmune diseases. Many of these diseases are of major clinical significance, such as rheumatoid arthritis and type I diabetes. Thus the industrial application and utility of the invention flow from these significant healthcare applications.

Phosphatidyl Inositol-3-Kinase (PI3-K)

PI3-K's are a family of enzymes having numerous different individual isoenzymes. In a broad aspect, the invention relates to the use of PI3-K inhibitors, preferably class I PI3K inhibitors, in the induction of Foxp3 expression. However, it is clear from our own data that inhibition of the class IB PI3 Kgamma does not induce Foxp3 expression, and that PI3-Kγ does not act via regulatory T cells. This observation is in contrast with the prior art teachings which say that PI3-Kγ can have modulatory effects. However, as disclosed herein, in fact PI3-Kγ is not exerting its effects by action in regulatory T cells, and therefore inhibition of or inhibitors of PI3-Kγ are specifically disclaimed from the present invention. Preferably references to PI3-K inhibitors should be construed as references to class IA PI3-K inhibitors which are not specific for PI3-Kbeta. Preferably references to PI3-K inhibitors should be construed as not referring to any compound which acts to inhibit PI3-Kγ activity.

Whether or not a compound acts to inhibit a particular PI3K activity, such as PI3-Kγ activity, may be easily determined. For example, one way in which inhibition of PI3-Kγ may be determined is set out in th examples. Moreover, it may be determined whether a compound is a PI3K isoform specific or selective inhibitor, such as a PI3-Kγ specific or selective inhibitor, by testing according to methods described herein or in the prior art. The standard test is to produce the kinase and to test it in vitro with the inhibitor in a titration experiment with different concentrations of inhibitor and a suitable test substrate capable of being phosphorylated by the kinase being tested. Furthermore, PI3K inhibitors are typically characterised with reference to their specificity by the manufacturer/supplier or in the literature connected with the compound of interest.

References to PI3-K should be construed as relating to PI3-K's, preferably class I PI3K's, preferably class IA PI3K's, preferably class IA PI3K's except for gamma, most preferably a class IA PI3-K selected from the group consisting of PI3-Kα, PI3-Kβ, PI3-Kδ.

It is further disclosed herein that PI3-Kβ has a limited role or no role in Foxp3 induction. Therefore, preferably the PI3-K is not PI3-Kβ, and preferably the PI3-K inhibitor is not specific or selective for PI3-Kβ.

Specifically, we show that inhibition of PI3-Kα or PI3-Kδ is particularly advantageous. Therefore, in a preferred embodiment, the PI3-K inhibitor is an inhibitor which is specific for or selective for PI3-Kα. In another preferred embodiment, the PI3-K inhibitor is an inhibitor which is selective for or specific for PI3-Kδ.

Target Cells

The target cells in which it is desired to produce Foxp3 expression may be any cells. Preferably the cells are haematopoietic cells, preferably the cells are cells of the T cell lineage, preferably the cells are thymocytes or lymphocytes, preferably the cells are a population of lymphocytes such as peripheral lymphocytes (e.g. peripheral blood lymphocytes) comprising a sub-population of mature T cells. Preferably the target cells are T cells, preferably mature naïve T cells. When the cells are thymocytes, preferably the techniques used are the same as for peripheral T cells.

Preferably the target cells are not CD8+ T cells. CD8+ T cells do not express Foxp3 after activation and PI3K inhibition. Suitably the target cell(s) do not comprise CD8+ T cells. Suitably the target cell(s) are depleted for CD8+ T cells, or are essentially free of CD8+ T cells. Suitably target cells are naïve T cells.

Preferably the target cells are not transgenic cells. Transgenic cells can be genetically unstable. Trasgenic cells can be subject to regulatory problems when contemplating their reintroduction to a subject. Preferably target cells are naturally occurring cells previously collected from a subject of interest.

When the cells to be treated only comprise a sub-population of target cells (T cells), e.g. when the treatment is conducted on peripheral lymphocytes, then clearly the term 'target cell' must be interpreted accordingly to refer to the T cells within the overall population of cells being treated. In other words, in working the invention it may be desired to treat a population of cells to induce Foxp3 expression when in fact only a sub-population of those cells are target cells. For example, a population of peripheral lymphocytes may comprise B cells, T cells and other cells. For convenience the whole population of peripheral lymphocytes may be treated, but of course it will be appreciated by the skilled reader that only a proportion of them (i.e. the T cells) are in fact target cells. Since the aim is typically to generate Tregs, the target cells will be non-Treg cells. Preferably the target cells are T cells which do not express Foxp3 before the treatment(s) of the invention.

Methods of Generating Regulatory T Cells

In a broad aspect, the invention relates to taking a population of one or more T cells, treating them with a PI3-K inhibitor, and obtaining regulatory T cells.

In slightly more detail, preferably the population of T cells are stimulated via the T cell receptor (TCR) or the TCR-associated CD3 complex of signalling proteins. In practice, TCR signal is in fact transmitted via the associated proteins. Thus, to stimulate via the TCR it is possible to target the actual TCR itself (e.g. antigen specific TCR targeting) or to target CD3 (e.g the TCR associated protein(s)). This stimulation is then preferably withdrawn. Following withdrawal of this stimulation, the cells are treated with a PI3-K inhibitor. Following incubation with the PI3-K inhibitor regulatory T cells are obtained. Specifically, treatment of the PI3-K inhibitor induces Foxp3 expression and this leads to a regulatory T cell fate or differentiation into a regulatory T cell.

Illustrative methods for producing this effect are provided in the examples.

The timing with regard to TCR stimulation can advantageously be manipulated to improve the effects. Preferably the T cells have been recently activated when they are treated with PI3-K inhibitor. Activation refers to stimulation via the T cell receptor. By "recent" is meant stimulation or activation within the preceding two days.

Best results are obtained when inhibitor treatment such as PI3-K inhibitor treatment is applied within 48 hours of activation. Preferably inhibitor treatment such as PI3-K inhibitor treatment is provided within 3-47 hours of stimulation, preferably within 47 hours of stimulation, preferably within 30 hours of stimulation, preferably at around 18 hours from stimulation, preferably at 18 hours from stimulation. Preferably inhibitor treatment such as PI3-K inhibitor treatment is provided at least 3 hours after stimulation, preferably at least 4 hours after stimulation, preferably more than 9 hours after stimulation, preferably at least 10 hours after stimulation, preferably about 18 hours after stimulation, preferably at 18 hours after stimulation. The technical benefits of these timings are optimisation and/or maximisation of the Foxp3 induction.

Preferably the time from stimulation is the time from withdrawal of signalling via the T cell receptor.

In a preferred embodiment, inhibitor treatment such as PI3-K inhibitor treatment is provided in a range of 3-47 hours from stimulation, preferably from 4-47 hours from stimulation, preferably from 4-30 hours from stimulation, preferably from 10-30 hours from stimulation, preferably from 12-25 hours from stimulation, preferably from 15-25 hours from stimulation, preferably from 17-19 hours from stimulation, preferably at around 18 hours from stimulation, preferably at 18 hours from stimulation. The technical benefits of these timings are optimisation and/or maximisation of the Foxp3 induction.

In a most preferred embodiment, the inhibitor treatment such as PI3-K inhibitor treatment is provided at a time of 10 to 22 hours after stimulation, preferably 12 to 20 hours after stimulation, preferably 12 to 18 hours after stimulation, preferably 17 to 19 hours after stimulation, preferably about 18 hours after stimulation, preferably 18 hours after stimulation. This has the advantage of excellent Foxp3 induction. Indeed, the technical benefit of these timings is illustrated in the examples section, e.g. with reference to FIG. 1C.

Regulatory T Cells

Regulatory T cells (sometimes referred to as Tregs) are an important component of a healthy immune system. Regulatory T cells are involved in keeping effector T cells in check, and in prevention of "self recognition" which can be a major factor in autoimmune disease.

Regulatory T cells have numerous acknowledged biomarkers known in the art. These include CD4+, CD25+, and Foxp3+. In particular, according to the present invention a regulatory T cell must show Foxp3 expression (Foxp3+).

A regulatory T cell must preferably display regulatory function. Exhibition of regulatory function may be determined by any suitable method known in the art. In particular, examples of such tests are set out in the example section. Specifically, the tests embodied in FIG. 3 are regarded as standard in vitro tests for regulatory T cell function.

In vivo it is widely believed that regulatory T cells need additional factors such as IL-2, TGFbeta, or IL-9 (such as mast cell derived IL-9) for their survival and/or the maintenance of their regulatory functions. Thus, in preferred embodiment, the invention relates to the induction of Foxp3 in T cells together with contacting those T cells with said lymphokines; contacting with said lymphokines may be accomplished by contacting with cells producing said lymphokines such as mast cells. In this embodiment, the cells producing said lymphokines (e.g. mast cells) may be provided in vivo in the subject being treated. It should be noted that PI3 KP110δ knockout animals do not have mast cell dependent responses, and show reduced Treg function.

PI3K/m-TOR/Akt Inhibitors

The PI3K inhibitors of the invention may be any compound or compounds capable of inhibiting PI3K, preferably class I PI3K, preferably class IA PI3K. In particular, the PI3K inhibitors may be biological macromolecules or may be small organic or inorganic compounds. Preferably the PI3K inhibitors are small organic compounds, preferably synthetic compounds.

Several small molecule PI3K inhibitors are under evaluation for clinical use—these are preferred inhibitors of the invention. Several small molecule inhibitors of PI3K are approved for clinical use—these are more preferred inhibitors of the invention.

Of course, some PI3-K inhibitors may act on more than one isoenzyme. If a PI3-K inhibitor happens to act upon one of the PI3-K subtypes which we disclose do not directly cause induction of Foxp3 expression, this does not exclude it from the present invention. The important characteristic of a PI3-K inhibitor as used herein is that it does act to inhibit one of the PI3-K isoenzymes which are disclosed as important for the induction of Foxp3 expression. Therefore, a PI3-K inhibitor according to the present invention must preferably display activity to inhibit the action of PI3-Kα and/or PI3-Kδ. If such an inhibitor also has a subsidiary effect on a different PI3-K isoenzyme such as PI3-Kβ or PI3-Kγ, such an inhibitor should not be regarded as excluded from the present invention. However, clearly it is preferably to choose the PI3-K inhibitor which has as specific an effect as possible in order to simplify administration and to avoid unwanted pleiotropic effects or side effects. Therefore, preferably the PI3-K inhibitor of the invention is specific for a given PI3-K isoenzyme. Preferably the PI3-K inhibitor of the invention is specific for PI3-Kα and/or PI3-Kδ. Preferably the inhibitor is specific for PI3-Kα. Preferably the inhibitor is specific for PI3-Kδ. Inhibitors which reduce the activity of both PI3-Kα and PI3-Kδ are particularly preferred; most preferred are inhibitors which reduce the activity of PI3-Kα and PI3-Kδ but do not reduce the activity of other isoenzymes such as PI3-Kγ and/or PI3-Kβ.

Most preferably the inhibitor is specific for PI3-Kalpha or delta, preferably the inhibitor is specific for PI3-Kalpha and delta, since these are the predominant activities in regulation of Foxp3.

Most preferred are PI3K inhibitors which are approved for clinical use and which inhibit PI3K alpha and/or PI3K delta. Even more preferred are such inhibitors which also do not reduce the activity of other isoenzymes such as PI3-Kγ and/or PI3-Kβ.

In contrast to bioactive peptides purified from biological sources as have been used in the prior art (e.g. TGF beta), small molecule inhibitors of PI3K can be produced synthetically and have superior pharmacological properties (analogous to the difference between insulin and oral antidiabetics). The use of synthetic PI3K inhibitor compounds, such as those with selectivity for individual PI3K isoenzymes, offers the technical advantage that side effects of bioactive peptides can be minimised or eliminated.

A new generation of PI3-K inhibitors has recently been characterised at the biochemical, structural, and biological level and shown to have selectivity for PI3-K isoenzymes in preference over an extensive range of other kinases (Knight et al., 2006 Cell vol 125 pp 733-747). Selective class IA PI3K inhibitors are preferred inhibitors of the invention. Preferred inhibitors are shown in the examples section; most preferred are the alpha and delta PI3K inhibitors of the examples section.

m-TOR inhibitors include rapamycin, wortmannin, and synthetic compounds such as PIK-90. Preferred m-TOR inhibitors are disclosed above and in the examples section. Most preferred is rapamycin.

Protein kinase B or Akt (PKB/Akt—for convenience this is referred to herein simply as 'Akt') is a serine/threonine kinase, which in mammals comprises three highly homologous members known as PKB alpha (Akt1), PKB beta (Akt2) and PKB gamma (Akt3). Akt inhibitors include the allosteric inhibitor Akti-1/2.

Rapamycin

Although inhibition of m-TOR signalling (i.e. rapamycin treatment) has been shown to contribute to expansion of Foxp3+ Tregs in the prior art, there is no teaching of induction of Foxp3 by rapamycin. The inventors are not aware of any link between m-TOR inhibition and Foxp3 induction in the art. Indeed, the present inventors have investigated this area using biologically relevant starvation/nutrient depletion induced reduction of m-TOR activity. These signals were shown to abolish pS6 as a demonstration of reduced m-TOR activity but do not lead to induction of Foxp3. This elegant dissection of the system illustrates that the methods of the invention provide a new approach to the induction of Foxp3 and further show that prior art approaches acting via m-TOR signalling to produce expansion of Foxp3+ cells do not in fact induce de novo expression of Foxp3 nor differentiation of Tregs.

Rapamycin is not a PI3K inhibitor. For example, it is demonstrated in the art that 'no protein kinase tested was inhibited significantly by rapamycin at 1 microM, a concentration 10-20-fold higher than that required to inhibit mTor in cell-based assays (Bioch. J. 351:95-105, 2000)', the standard work on inhibitor specificity.

Combinations

Once Foxp3 expression has been induced according to the invention, it may be advantageous to combine the methods taught herein with methods promoting expansion of those cells. Thus, in a preferred embodiment, preferably regulatory T cells in which Foxp3 expression has been induced are subsequently expanded. Preferably this is accomplished by rapamycin treatment. In particular, this may be accomplished as in Battaglia et al 2005 Blood Volume 105 page 4743.

Further Applications

The invention finds broad application in clinical settings where the de novo generation of Treg cells is desirable, such as the prevention and/or the treatment of autoimmune diseases.

m-TOR inhibition may be important for maintenance of in vitro regulatory function.

The invention finds application in the induction of regulatory T cells for a specific antigen. In this embodiment, the antigen is first selected and then Foxp3 induction takes place in T cells capable of responding to the specific antigen.

Regulatory T cells control immune systems. In particular, they hold T effector cells in check. Deficiencies in regulatory T cells are associated with auto-immune diseases such as rheumatoid arthritis. Thus, by making regulatory T cells, typically by induction of Foxp3 expression as disclosed herein, such immune damage can be stopped, prevented or reduced.

The invention may advantageously be applied to the generation of regulatory T cells in vitro. In the prior art, this has been accomplished by treatment with TGFβ. The present invention provides a convenient alternative to this method. Furthermore, the invention provides the advantage of avoiding exposure to the bioactive TGFβ peptide.

In particular, the invention finds application in the ex vivo production of regulatory T cells. In this embodiment, a population of T cells would be taken from a patient. These would then be treated according to the methods of the present invention to induce regulatory T cells. These regulatory T cells may then be reintroduced into that patient to provide the therapeutic effect.

The invention finds application in immuno suppression. In particular, immuno suppression may be applied following organ transplantation or graft versus host disease.

The invention also finds application in autoimmune disease generally. In particular, the invention finds application in autoimmune diseases such as gastritis, thyroiditis, inflammatory bowel disease, ulcerative colitis, autoimmune diabetes, multiple sclerosis or other autoimmune diseases.

Furthermore, the invention finds application in suppression of allograft rejection, and examples of arthritis such as rheumatoid arthritis or collagen induced arthritis. Moreover, the invention finds application in combating certain cancers, specifically those cancers which are themselves comprised of lymphocytes such as B-cell malignancies (e.g. leukaemia, lymphoma etc.) as discussed herein.

In another embodiment, preferably methods of the invention are in vitro. Preferably methods of the invention do not involve the human or animal body.

Suitably references to induction of Foxp3 expression should be understood to mean induction of de novo Foxp3 expression. Suitably enhancement of existing Foxp3 expression, or expansion of cells already expressing Foxp3, are not part of the present invention. Suitably the invention relates to producing Foxp3 expression in cell(s) which were not expressing Foxp3 before the treatments/methods of the invention. Without wishing to be bound by theory, expression of Foxp3 is necessary and sufficient for Treg production from an appropriate target cell. Thus incubation of a cell cause to express Foxp3 de novo according to the present invention leads to Treg production.

Certain aspects of the invention may be understood with reference to the following numbered paragraphs:

1. A method for generating a regulatory T-cell comprising treating a stimulated T cell with phosphatidyl inositol 3 kinase (PI3K) inhibitor wherein said inhibitor inhibits PI3K alpha and/or PI3K delta.

2. A method for generating a regulatory T-cell comprising
   (i) stimulating a T cell
   (ii) optionally withdrawing said stimulation
   (iii) inhibiting signalling via PI3K alpha or PI3K delta or m-TOR or Akt in said T cell.

3. A method of treating a subject in need of regulatory T cell(s) comprising
   (i) removing a sample comprising a T cell from a subject
   (ii) stimulating said T cell
   (iii) optionally withdrawing said stimulation
   (iv) inhibiting signalling in said T cell via PI3K alpha or PI3K delta or m-TOR or Akt; and
   (v) reintroducing said T cell to said subject 4. A method of inducing Foxp3 expression in a previously stimulated T cell comprising inhibiting signalling in said T cell via PI3K alpha or PI3K delta or m-TOR or Akt.

5. A method of inducing Foxp3 expression in a T cell comprising
   (i) stimulating a T cell
   (ii) optionally withdrawing said stimulation; and
   (iii) inhibiting signalling in said T cell via PI3K alpha or PI3K delta or m-TOR or Akt.

6. A method according to any preceding paragraph wherein stimulating said T cell comprises stimulating said T cell via the T cell receptor (TCR).

7. A method according to any preceding paragraph wherein inhibiting signalling via PI3K alpha or PI3K delta comprises contacting said cell with PI3K inhibitor, and wherein said inhibitor inhibits PI3K alpha and/or PI3K delta.

8. Use of a PI3K inhibitor in the induction of differentiation of a T cell into a regulatory T cell wherein said inhibitor inhibits PI3K alpha and/or PI3K delta.

9. Use of a PI3K inhibitor in the induction of Foxp3 expression wherein said inhibitor inhibits PI3K alpha and/or PI3K delta.

10. Use of a PI3K alpha inhibitor or a PI3K delta inhibitor for the manufacture of a medicament for deficiency of regulatory T cells.

11. PI3K alpha inhibitor for use in the treatment of a deficiency of regulatory T cells.

12. PI3K delta inhibitor for use in the treatment of a deficiency of regulatory T cells.

13. A kit comprising
    (i) a TCR stimulant; and
    (ii) an inhibitor of PI3K alpha or delta.

14. A kit according to paragraph 13 wherein said TCR stimulant comprises anti-TCR and anti-CD28 antibody.

15. A kit according to paragraph 13 or paragraph 14 further comprising an m-TOR inhibitor.

16. A kit according to paragraph 15 wherein said m-TOR inhibitor is rapamycin.

17. A kit according to any of paragraphs 13 to 16 further comprising an Akt inhibitor.

18. A method according to any of paragraphs 1 to 7, a use according to any of paragraphs 8 to 10, and inhibitor according to paragraph 11 or paragraph 12, or a kit according to any of paragraphs 13 to 17 wherein said PI3K inhibitor comprises LY294002.

Figure 1:
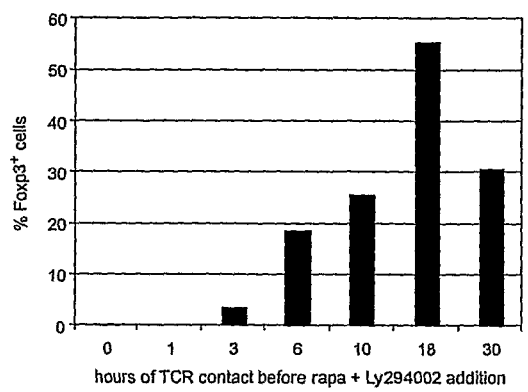
FIG. 1 shows TCR signal deprivation induces Foxp3 expression by newly activated T cells in synergy with inhibitors of the PI3-K/mTOR pathway
a) naive CD62LhiCD4+CD25− LN T cells were stimulated with plate bound anti TCR and anti CD28 for 18 hours and cultured for an additional two days in the presence of TCR antibody (continued TCR signalling) or in the absence of TCR antibody (TCR signal deprivation). The expression of Foxp3 RNA was assessed by real time RT-PCR (mean±SD, n=3).

b) naive CD4 T cells were labelled with CFSE and stimulated with plate bound anti TCR and anti CD28 as in a) and transfered to the indicated conditions after 18 hours. The expression of Foxp3 protein was evaluated by intracellular staining 2 days later. CFSE profiles are shown for Foxp3– and Foxp3+ cells.

c) Foxp3 induction is most effective 18 hours after the activation of naive CD4 T cells.

FIG. 2 shows TCR signaling controls mTOR activity in newly activated CD4 T cells a) naive LN T cells were stimulated with plate bound anti TCR and anti CD28 for 1 or 18 hours, or for 1 hour with anti CD28 alone (no TCR signaling). Phosphorylation of S6 ribosomal protein was determines at the single cell level using intracellular staining and flow cytometry.

b) naive LN cells were activated as in a). After 18 hours, rapamycin (25 nM) or Ly294002 (10 µM) were added for one additional hour, or the cells were cultured for the indicated time in the absence of anti TCR. pS6 levels were determined as in a).

FIG. 3 shows induction of Foxp3 by TCR signal deprivation and PI3K/mTOR inhibitors is stable and results in the acquisition of regulatory function.

a) Foxp3 expression was induced in naive CD4 T cells by TCR signal deprivation, rapamycin and Ly294002 and monitored over time. The cells were re-stimulated every 7 days in the presence of IL-2.

b) naive CD4 T cells were activated for 18 hours and cultured for an additional 2 days either with anti-TCR (control, <1% Foxp3+) or without anti-TCR and in the presence of rapamycin and Ly294002 (Foxp3 induced, 28% Foxp3+). Graded numbers of Foxp3 induced or control cells were added to fresh, CFSE labelled CD4 LN T cells in the presence of APC and soluble anti CD3 and the effect on cell division (CFSE profile) was recorded 48 h later.

FIG. 4 shows Foxp3 expression in response to TCR signal deprivation and PI3-K/mTOR inhibition in vivo a) naive CD4 T cells were labelled with CFSE and stimulated with plate bound anti TCR and anti CD28 and transfered i.v. to syngeneic, immunocompetent hosts after 18 hours with or without rapamycin and Ly294002 i.p. as indicated. The expression of Foxp3 protein by endogeous (CFSE−) and transfered (CFSE+, the inset displays a greater number of events) CD4+ spleen cells was evaluated 2 days later by intracellular staining.

b) summary of 11 transfer experiments at 18 or 48 hours

FIG. 5 shows differential involvement of p110 isoenzymes in Foxp3 induction Naive LN cells were activated as in FIG. 1 and PI3-K inhibitors were added after 18 hours. The p110 isoform specificity of each inhibitor at the concentration used is shown (left panel). The percentage of Foxp3+ cells in cultures deprived of TCR signaling (14% in this experiment) was subtracted to indicate the net effect of PI3-K inhibitors (red Δ values in each scatter plot). Cells were labeled with CFSE prior to activation to monitor cell division (left panel). For each inhibitor, S6 ribosomal protein phosphorylation was determined by intracellular staining after 90 minutes and the percentage of pS6+ cells is shown (black, mean±SD, n=3-5 except TGX-115, n=1, right panel). The percentage of Foxp3+ cells is shown after subtracting the percentage of Foxp3+ cells in cultures deprived of TCR signaling (red, mean±SD, n=4-12). IC50 values determined in vitro (Camps et al., 2005; Knight et al., 2006) are indicated for relevant enzymes (right panel).

FIG. 6. Foxp3 induction by inhibitors of PI3K/mTOR signaling is independent of TGFβ a) naive LN T cells were activated in serum free AIM-V medium (Invitrogen) for 18 hours and whole cell extracts were subjected to SDS gel electophoresis and western blotting after exposure of the cells to TGFβ (1 ng/ml) for (90 minutes, lane 1), TCR signal deprivation (90 minutes, lane 2), or TCR signal deprivation plus rapamycin and Ly294002 (90 minutes, lane 3 or 8 hours, lane 4). The blot was sequentially probed with anti pSmad2 (S465/467) and anti Smad2/3.

b) naive LN T cells activated as in a) were deprived of TCR signals and TGFβ and PI3-K/mTOR inhibitors were added as indicated below the graph. The percentage of Foxp3 expressing cells was determined 24-48 hours later. Cultures were supplemented with neutralising anti TGFβ (R&D Systems, 3 µg/ml) or the Smad kinase inhibitor SB431542 (Sigma, 20 µM). Foxp3 expression in TCR signal deprived cultures (9.2±5.6%, n=6) was subtracted. Shown is Foxp3 expression in the presence of anti TGFβ (dark grey bars) or SB431542 (light grey bars) normalisesd to control cultures (100%, black bars; TGFβ 22.3±7.0%, n=9; PIK90 36.0±12.9%, n=7; PI-103 35.1±3.8%, n=8; Ly294002 21.5±4.0%, n=4 and rapamycin 28.6±9.0%, n=4). ND: not done.

Figure 7:
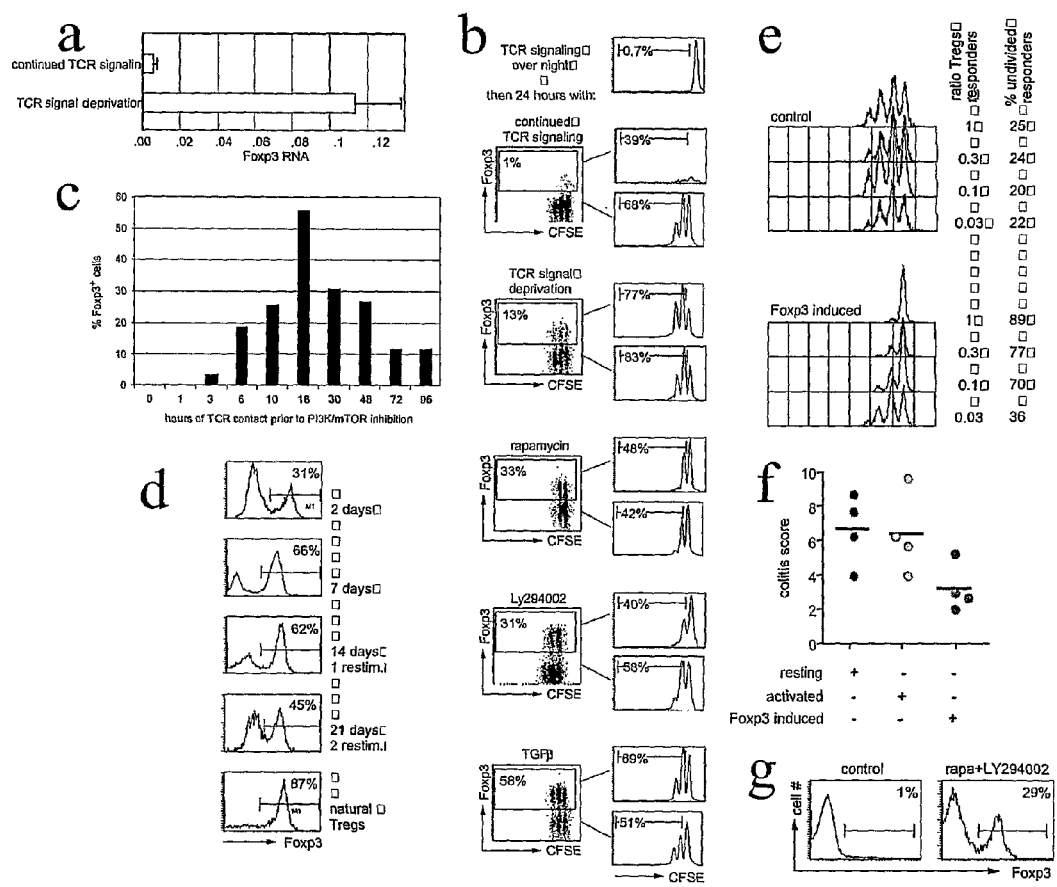

FIG. 7 shows TCR signal deprivation and inhibitors of the PI3K/mTOR pathway induce Foxp3 expression by newly activated T cells.

a) naive $CD62L^{hi}CD4^+CD25^-$ LN T cells were stimulated with plate bound anti-TCR and soluble anti-CD28 for 18 hours and cultured for an additional two days with TCR antibody (continued TCR signaling) or without TCR antibody (TCR signal deprivation). The expression of Foxp3 RNA was assessed by real time RT-PCR (mean±SD, n=3).

b) naive CD4 T cells were labelled with CFSE and stimulated with plate bound anti TCR and anti CD28 as in a) and transfered to the indicated conditions after 18 hours. The expression of Foxp3 protein was evaluated by intracellular staining 2 days later. Cell recovery was between 67 and 108% of input. CFSE profiles are shown for Foxp3− and Foxp3+ cells.

c) naive LN CD4 T cells were activated as in a) for the indicated number of hours, after which the cells were deprived of TCR signals and exposed to rapamycin and LY294002. The percentage of Foxp3 expressing cells was determined 2 days later (mean of 2 experiments).

d) Foxp3 expression was induced in naive CD4 T cells by TCR signal deprivation, rapamycin and LY294002. The cells were re-stimulated weekly in the presence of IL-2 and Foxp3 expression was monitored. Natural Treg cells are shown for comparison.

e) naive CD4 T cells were activated for 18 hours and cultured for an additional 2 days either with anti-TCR (control, <1% Foxp3+) or without anti-TCR and in the presence of rapamycin and LY294002 (Foxp3 induced, 28% Foxp3+). Graded numbers of Foxp3 induced or control cells were added to fresh, CFSE labelled CD4 LN T cells in the presence of APC and soluble anti CD3 and the effect on cell division (CFSE profile) was recorded 48 h later.

f) naive $CD45RB^{hi}CD4^+CD25^-$ LN cells were transferred intravenously into syngeneic Rag deficient recipients, either freshly isolated ex vivo, activated under control conditions with continued TCR activation, or deprived of TCR signals and treated with rapamycin and LY294002 after 18 hours. Colitis scores were determined after eight weeks.

g) CD4 single positive, CD25 negative thymocytes were activated, TCR signals were withdrawn, rapamycin/LY294002 added after 18 hours and Foxp3 expression analysed 2 days later as in b).

Figure 8:
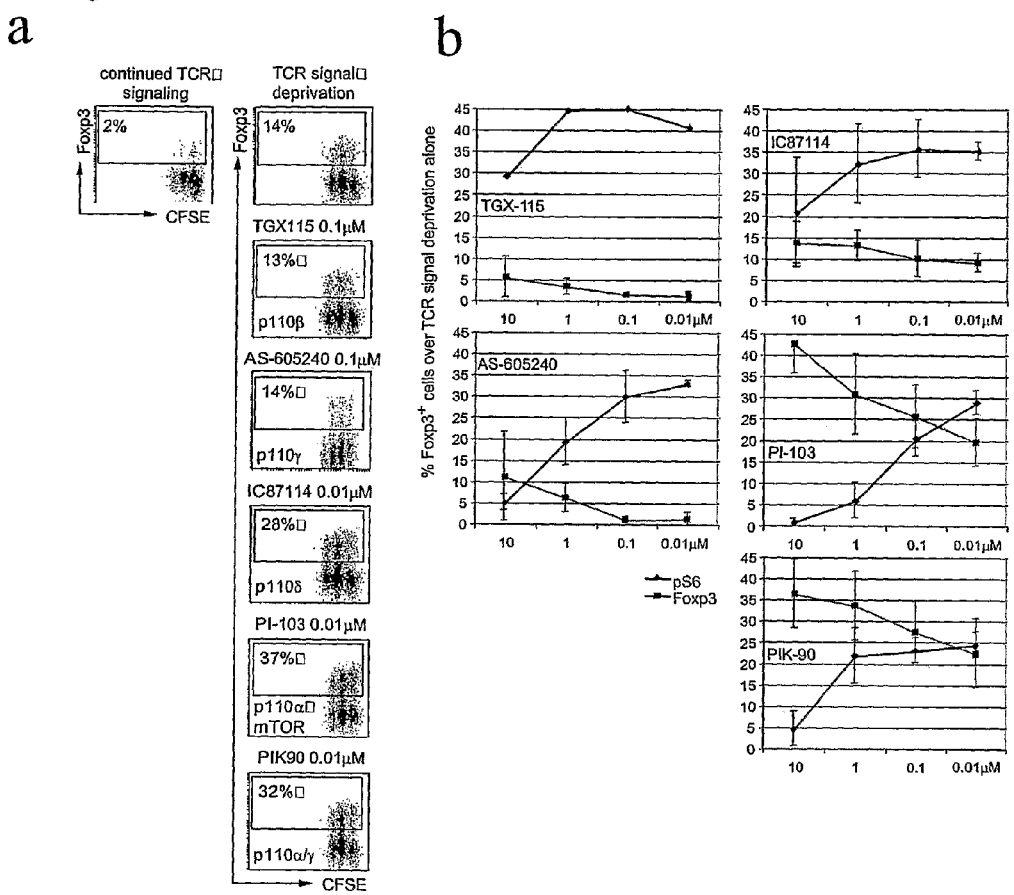

FIG. 8 shows differential involvement of p110 isoenzymes in Foxp3 induction a) naive LN cells were activated as in FIG. 1 and PI3K inhibitors were added after 18 hours. The p110 isoform specificity of each inhibitor at the concentration used is shown alongside the percentage of Foxp3$^+$ cells.

b) The percentage of pS6$^+$ cells was determined by intracellular staining at 90 min (black, mean±SD, n=3-5 except TGX-115, n=1, right panel). Shown is the increase in Foxp3$^+$ cells over that in cultures deprived of TCR signaling (red, mean±SD, n=4-12). IC$_{50}$ values determined in vitro are indicated for relevant enzymes.

Figure 9:
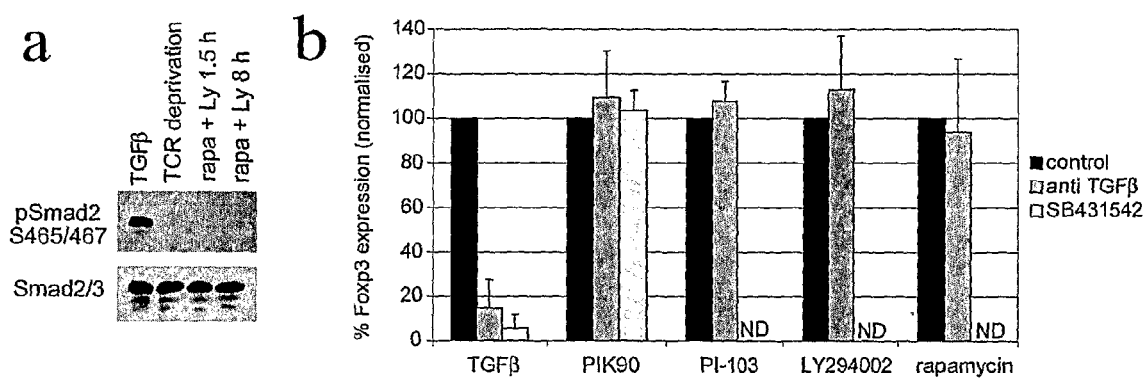
Figure 10:
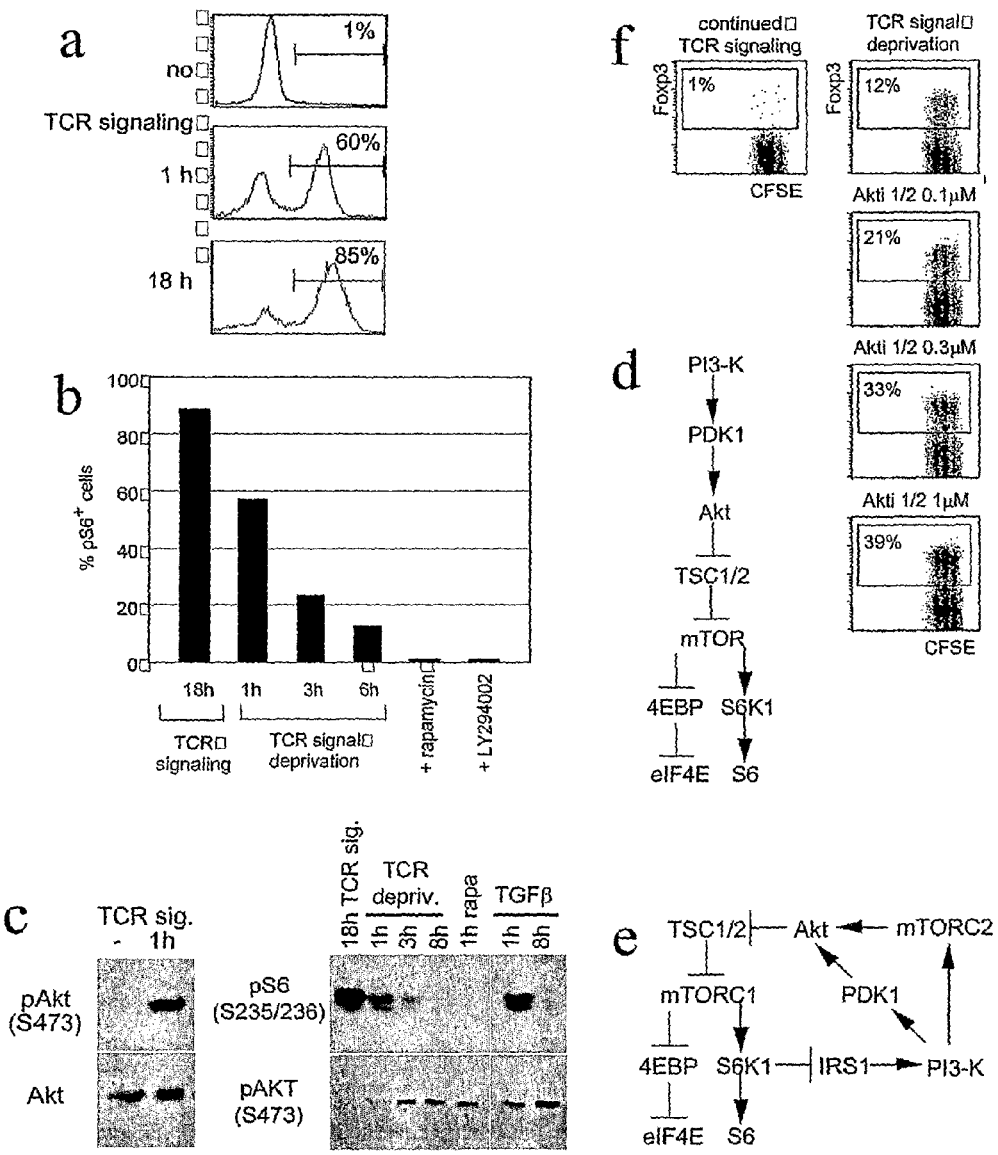

FIG. 9 shows Foxp3 induction by PI3K/mTOR signaling is independent of TGFβ.

a) naive LN T cells were activated in serum free AIM-V medium for 18 hours and whole cell extracts were subjected to SDS gel electophoresis and immunoblotting after exposure of the cells to TGFβ (1 ng/ml) for (90 minutes, lane 1), TCR signal deprivation (90 minutes, lane 2), or TCR signal deprivation, rapamycin and LY294002 (90 minutes, lane 3 or 8 hours, lane 4). The blot was stripped and probed probed with anti pSmad2 (S465/467) and anti Smad2/3.

b) naive LN T cells activated as in a) were deprived of TCR signals and TGFβ and PI3K/mTOR inhibitors were added as indicated. Cultures were supplemented with neutralising anti TGFβ (3 μg/ml) or the Smad kinase inhibitor SB431542. Shown is Foxp3 expression in the presence of anti TGFβ (dark grey bars) or SB431542 (light grey bars) determined 2 days later and normalisesd to control cultures without anti TGFβ and SB431542 (black bars; TGFβ 22.3±7.0%, n=9; PIK90 36.0±12.9%, n=7; PI-103 35.1±3.8%, n=8; LY294002 21.5±4.0%, n=4 and rapamycin 28.6±9.0%, n=4). ND: not done. Foxp3 expression in TCR signal deprived cultures (9.2±5.6%, n=6) was subtracted FIG. 10 shows the impact of TCR signaling on the PI3K/mTOR/Akt network in newly activated CD4 T cells.

a) naive LN CD4 T cells were stimulated with plate bound anti TCR and anti CD28 for 1 or 18 hours, or for 1 hour with anti CD28 alone (no TCR signaling). S6 phosphorylation was determined by intracellular staining and flow cytometry.

b) naive LN cells were activated as in a). After 18 hours, rapamycin (25 nM) or LY294002 (10 μM) were added for one additional hour, or the cells were cultured for the indicated time in the absence of anti TCR. pS6 levels were determined as in a).

c) immunoblotting confirmed declining pS6 in response to TCR signal deprivation and rapamycin detected at the single cell level in b). TGFβ also reduced pS6.

pAkt (S473) was visible 1 hour, not 18 hours after T cell activation but reappeared in response to TCR signal deprivation, rapamycin, and TGFβ.

d) pathway model of the PI3K/mTOR axis. PI3K activates Akt via PDK1, Akt inhibits TSC1/2, this activates mTOR, relieves translational inhibition via 4EBP/eIF4E and stimulates ribosomal activity via S6K1/eIF4E.

e) network models of the PI3K/mTOR axis distinguishes mTORC1 and mTORC2. mTORC1-dependent S6K1 activity blocks the activation of mTORC2 by PI3K via IRS 1. Akt activity depends on both PDK1 (T308) and mTORC2 (S473) (Jacinto et al., 2006; Sabatini, 2006).

f) Akt inhibition by Akti 1/2 induces Foxp3 expression. Naive CD4 T cells were activated and Foxp3 expression was evaluated as in FIG. 1.

Figure 11:
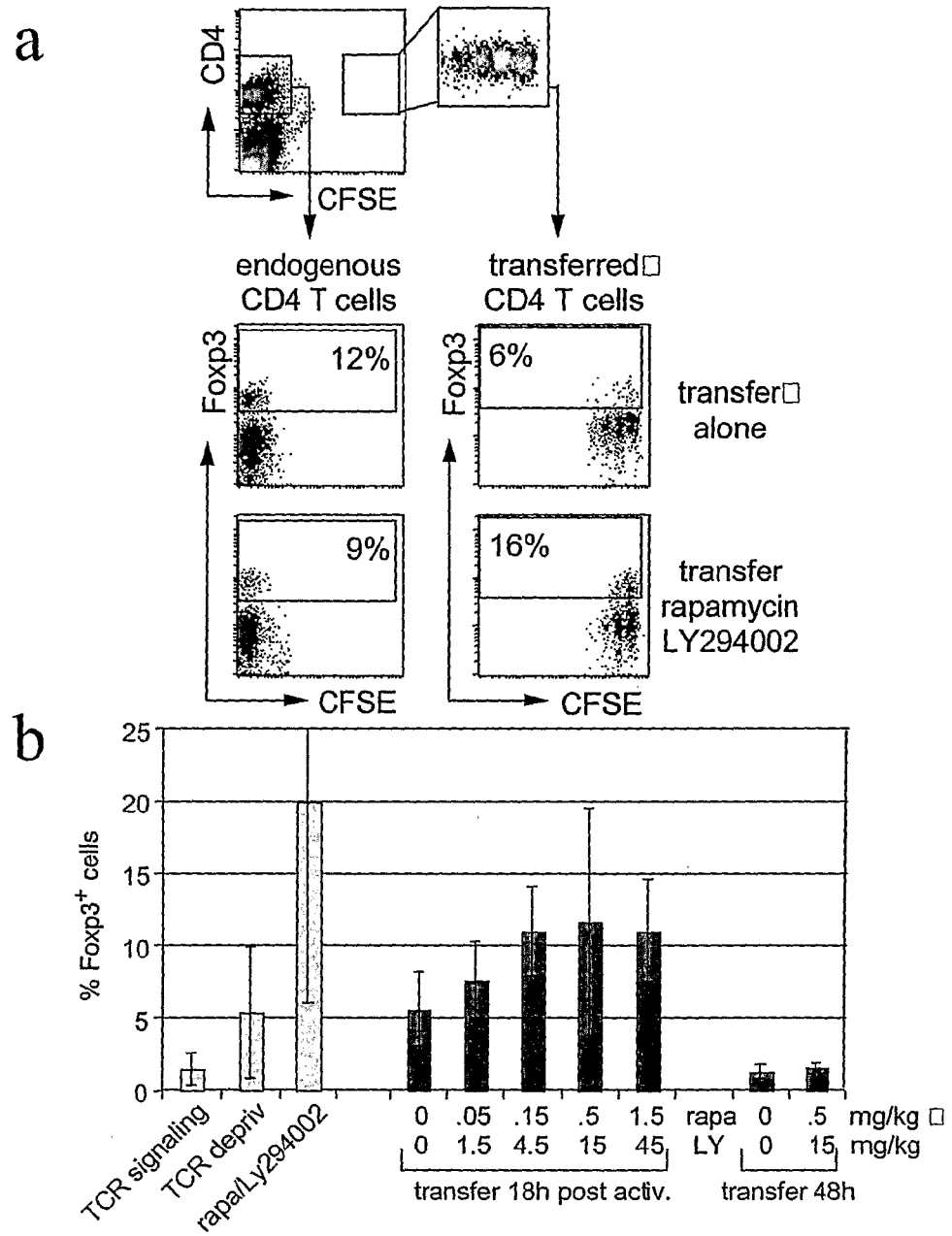

FIG. 11 shows Foxp3 expression in response to TCR signal deprivation and PI3K/mTOR inhibition in vivo.

a) to mimic TCR signal deprivation, CFSE labelled CD62L$^{hi}$CD4$^+$CD25$^-$ LN cells were activated and then transferred intravenously to syngeneic, fully immunocompetent hosts (2-4×10$^6$ cells per recipient) with or without intraperitoneal rapamycin (0.5 mg/kg) and LY294002 (15 mg/kg). Foxp3 expression by endogenous (CFSE$^-$) and transfered (CFSE$^+$) CD4 spleen cells was assayed two days later. With 5.3±4.6% (n=11) the frequency of Foxp3$^+$ cells recovered was 3 times higher than in the original inocula (1.5±1.1%). When cell transfer was accompanied rapamycin and LY294002 i.p., the frequency of Foxp3$^+$ cells increased further while Foxp3 expression among endogenous (CFSE$^-$) T cells did not change, demonstrating selectively toxicity to conventional, but not to Foxp3$^+$ CD4 T cells.

b) summary of 11 transfer experiments. To address whether the increase in Foxp3 expressing cells was due to the selective recovery of Foxp3$^+$ CD4 T cells or to Foxp3 induction we transferred CFSE labelled CD62L$^{hi}$CD4$^+$CD25$^-$ LN cells after 48 hours of activation, a time when TCR deprivation no longer efficiently induced Foxp3 expression in vitro (see FIG. 1c). Under these conditions, 1.3±0.5% of CFSE$^+$ cells expressed Foxp3 after transfer (n=4) and 1.6±0.3% of CFSE$^+$ cells after transfer in the presence of rapamycin and LY294002 (n=3).

Figure 12:
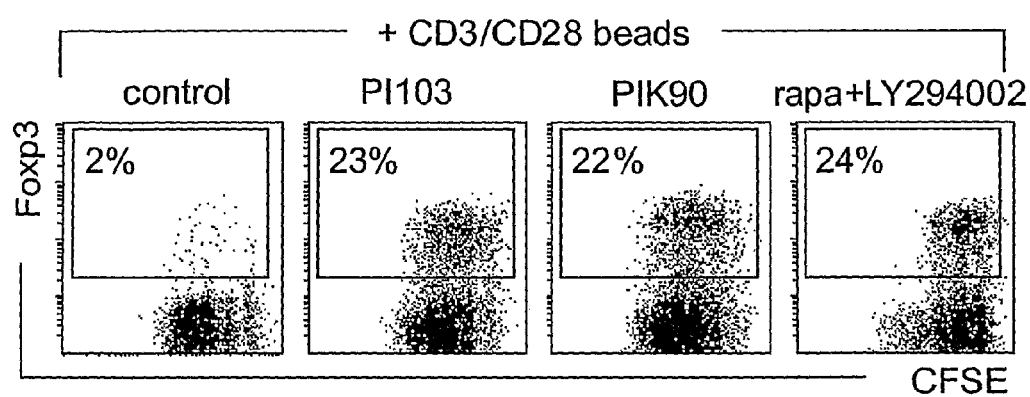

FIG. 12 shows Foxp3 induction by PI3K/mTOR inhibitors in the presence of continued availability of TCR ligands. Naive CD4 T cells were activated with CD3/CD28 beads (Dynal, 4 μl/10$^6$ cells). The indicated PI3K/mTOR inhibitors were added (1 μM) at 18 hours without removing the beads and Foxp3 expression was assessed two days later.

Figure 13:
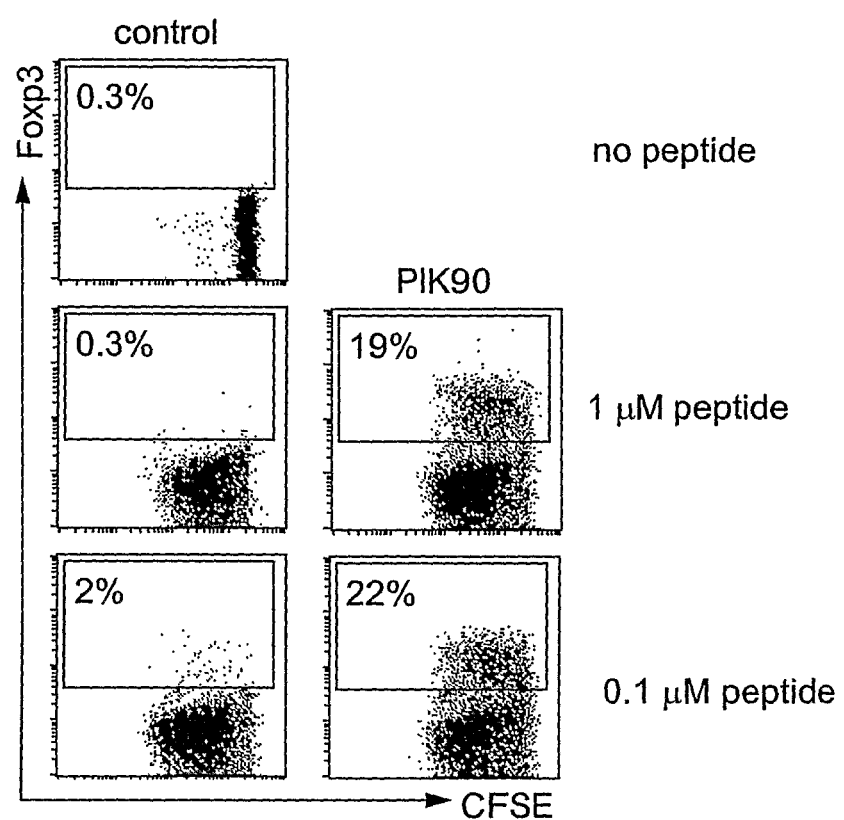

FIG. 13 shows Foxp3 induction in response to physiological TCR ligands and PI3K/mTOR inhibition.

CD4 LN cells from Rag1 deficient H2$^b$ AND TCR transgenic mice were labeled with CFSE and cultured with BM-derived B 10.BR (H2$^k$) antigen presenting cells pre-loaded with the indicated concentrations of pigeon cytochrome-C peptide 81-104. PIK90 (1 μM) was added after 18 hours without removing the antigen presenting cells or the antigenic peptide. Foxp3 expression was analysed two days later.

The invention is now described by way of example. These examples are intended to be illustrative, and are not intended to limit the appended claims.

EXAMPLES

Materials and Methods

Mouse strains, cell sorting and culture Animal work was carried out according the Animals (Scientific Procedures) Act, UK. Lymph node (LN) cells were stained, analysed and sorted by flow cytometry as described (Cobb et al 2005 J. Exp. Med. 201: 1367-1373). Intracellular staining for Foxp3 protein was done as advised by the manufacturers (eBiosciences.com). The phosphorylation syatus of S6 ribosomal protein was determined using anti pS6 Ser235/236 (Cellsignaling cat.no. 2211, http://www.cellsignal.com) using the eBioscience Foxp3 staining kit and anti rabbit IgG-FITC or IgG-Cy5 (Jackson Immunoresearch). For induction of Foxp3 expression, sorted LN CD4+ CD25− CD62Lhi T cells were cultured at 1-3×10⁶/ml with plate bound anti-TCRβ. (H57, Pharmingen, 200 ng/ml) and anti-CD28 (2 μg/ml, Pharmingen). After 18 hours the cells were either left in place for continued TCR stimulation or moved to uncoated wells with the indicated additives. To assess regulatory function, CD4 T cells cultured as indicated were titrated into round bottom wells containing either 1×10⁵ CFSE labeled total LN cells or 5×10⁴ CFSE labeled CD4⁺ CD25⁻ T cells and 1×10⁵ mitomycin-C treated (25 μg/ml, 20 min, 37° C.) T cell depleted splenocytes with the indicated concentrations of anti CD3 (2C11, Pharmingen). CD4 T cell CFSE profiles were recorded between 48 and 72 hours later.

Adoptive transfer experiments. To assess the impact of TCR signal deprivation and PI3-K/mTOR inhibition in vivo, BALB/c CD4+CD25– CD62Lhi LN T cells were labeled with CFSE, activated for 18 hours as above, and transfered i.v. into untreated syngeneic recipients (2-4×106 cells per recipient). Rapamycin and Ly294002 were given i.p. as indicated. Splenocytes were stained for CD4 and Foxp3 48 hours later and Foxp3 expression was determined for endogenous (CFSE–) and for transfered (CFSE+) CD4+ cells.

RT-PCR and northern blots. Total RNA was isolated using RNAbee (Tel-Test, Friendswood, Tex.) and reverse transcribed. Real-time PCR analysis was carried out on an Opticon™DNA engine (MJ Research Inc.; 95° C. for 15 min followed by 40 cycles of 94° C. for 15 s, 60° C. for 30 s and 72° C. for 30 s with a plate read at 72° C.) and normalised to the geometric mean of Ywhaz (tyrosine 3-monooxygenase/tryptophan 5-monooxygenase activation protein, zeta polypeptide) and Ube2L3 (ubiquitin conjugating enzyme E2L3) as described (Cobb et al 2005 ibid.). Primer sequences (5' to 3')

```
Ywhaz forward:
                                    (SEQ ID NO. 1)
GTTGTAGGAGCCCGTAGGTCAT Ywhaz reverse:
                                    (SEQ ID NO. 2)
TCTGGTTGCGAAGCATTGGG Ubc forward:
                                    (SEQ ID NO. 3)
AGGAGGCTGATGAAGGAGCTTGA Ubc reverse:
                                    (SEQ ID NO. 4)
TGGTTTGAATGGATACTCTGCTGGA Foxp3 forward:
                                    (SEQ ID NO. 5)
ACTCGCATGTTCGCCTACTTCAG Foxp3 reverse:
                                    (SEQ ID NO. 6)
GGCGGATGGCATTCTTCCAGGT
```

Example 1

Withdrawal of TCR Signal Induces Foxp3 Expression in Newly Activated T Cells

Naive CD4+CD25– cells were stimulated with plate bound anti-TCR(H57) and anti-CD28 for 18 hours and then transfered (in their original medium) to plates not coated with TCR antibodies. 48 hours later, real time RT-PCR showed elevated levels of Foxp3 RNA in cells deprived of TCR signals compared to controls exposed to continued TCR signaling (FIG. 1a). Intracellular staining showed the expression of Foxp3 protein in a sizeable fraction of newly activated CD4 T cells deprived of TCR signals (10.8±7.6% n=30) (FIG. 1b), but not in cells left in contact with TCR antibody (1.0±0.8% n=21).

Example 2

Inhibition of the PI3K/mTOR Pathway Promotes Foxp3 Expression in Newly Activated T Cells To identify relevant signaling pathways for the induction of Foxp3 we screened activators and inhibitors of signal transduction pathways. These included inhibitors of calcineurin, which block the nuclear translocation of NFAT (cyclosporin A and FK-506), activators and inhibitors of relevant MAPKs (mitogen activated kinases, including JNK/SAPK/p38 and upstream kinases), a wide range of inhibitors and pseudosubstrates of PKC isoenzymes, GSK3 (glycogen synthase kinase-3), HIF-1 (hypoxia inducible factor), Notch (using the -secretase inhibitor L-685458) and BMP (bone morphogenetic proteins, which are relatives of TGFβ). None of these detectably enhanced the expression of Foxp3 initiated by TCR signal deprivation. In contrast, inhibitors of PI3K and mTOR markedly potentiated Foxp3 induction. The immunosuppressive macrolide antibiotic rapamycin induced the expression of Foxp3 in 26.8±14.4% of cells within 24-48 hours (n=30, FIG. 1b). Similarly, the PI3K inhibitors Ly294002 (2-(4-Morpholinyl)-8-phenyl-4H-1-benzopyran-4-one) and Wortmannin induced Foxp3 (26.9±11.4%, n=25 for Ly294002, FIG. 1b and 17.3±5.3%, n=3, for Wortmannin). The control compound Ly303511 (2-piperazinyl-8-phenyl-4H-1-benzopyran-4-one) is structurally very similar to Ly294002 but does not inhibit PI3-K due to a single atom substitution in the morpholine ring. Ly303511 did not affect Foxp3 expression in our system (6.6±3.0%, n=7). Rapamycin and Ly294002 were maximally effective when used in combination with TCR signal deprivation 18 hours after the activation of naive CD4 T cells, before cell division had occurred (see below). TCR signaling was required for PI3K/mTOR inhibitors to induce Foxp3, and co-stimulation markedly enhanced the efficiency of Foxp3 induction (from 3 to 9% for TCR signal withdrawal, from 7 to 46% for TGFβ, from 10 to 25% for rapamycin and from 4 to 44% for Ly294002, average of two experiments. As a positive control, TGF induced Foxp3 in 46.0±15.1% of cells deprived of continued TCR signaling (n=30, FIG. 1b). To address whether the increased frequency of Foxp3 expressing cells was due to the selective expansion of preexisting Foxp3+ cells, we labelled naive CD4 T cells with CFSE prior to their activation. No cell division had occurred by 18 hours after activation, at the time the cells were placed in the indicated culture conditions (FIG. 1b). Twenty-four hours later, between 67 and 108% of input cells were recovered. Despite substantially enhancing the frequency of Foxp3 expressing cells, rapamycin and Ly294002 resulted in a slight reduction in the number of cell division, ruling out selective expansion as an explanation for the increased frequency of Foxp3 expressing cells in response to TCR signal deprivation and PI3K/mTOR inhibitors.

Inhibition of PI3-K/mTOR was less effective at inducing Foxp3 at later time points and once cell division had occurred (FIG. 1c).

Example 3

TCR Signalling Controls mTOR Activity in Newly Activated CD4 T Cells

To monitor the activity of the PI3K/mTOR axis in response to TCR signaling, TCR signal withdrawal and treatment with rapamycin and Ly294002, we analysed the level of phosphorylated S6 ribosomal protein (pS6), the target of p70 S6 kinase, which is directly regulated by mTOR. Intracellular staining for pS6 showed at the single cell level that TCR signaling (plate bound H57, 300 ng/ml) combined with anti-CD28 induced high levels of S6 phosphorylation in the majority of naive CD4 T cells (FIG. 2a). Anti-CD28 alone had no effect (FIG. 2a, top panel). S6 phosphorylation persisted in the presence of continued TCR signaling, but was completely removed by rapamycin (25 nM) or Ly294002 (10 g/ml) within one hour (FIG. 2b). pS6 declined more gradually when naive CD4 T cells that had been activated for 18 hours with plate bound H57 and anti CD28 were deprived of TCR signals (FIG. 2b). Hence, Foxp3 induction occurs in response to manipulations that reduce S6 phosphorylation. Importantly, however, reduced S6 phosphorylation is not sufficient for Foxp3 induction. In particular, the inhibition mTOR by nutrient deprivation of newly activated CD4 T cells fails to induce Foxp3 expression.

Example 4

Induction of Foxp3 by TCR Signal Deprivation and PI3K/mTOR Inhibitors is Stable and Results in the Acquisition of Regulatory Function As described above, Foxp3 expression was induced within 24-48 hours in response to TCR signal deprivation and PI3-K/mTOR inhibitors. We next examined the stability of Foxp3 expression and the functional competence of the Foxp3 induced cells, since transient upregulation of Foxp3 without regulatory function has been described in human CD4 T cells. Foxp3 was robustly expressed by day 7 after induction and expression was mitotically heritable, since it was stably maintained through several rounds of re-stimulation in IL-2 (FIG. 3a). To assess whether the induction of Foxp3 by PI3K/mTOR inhibition results in regulatory T cell function, CD62LhiCD4+CD25− LN cells were activated, deprived of TCR signals and cultured in the presence of rapamycin and Ly294002. Graded numbers of the resulting population (28% Foxp3+ by intracellular staining) were added to fresh, CFSE labelled CD4 LN T cells and efficiently blocked their response to soluble anti CD3 (2C11, 1 g/ml) as assessed by the cell division profile (FIG. 3b, top panel). In contrast, control cells (<1% Foxp3+) did not block anti CD3-induced division of CFSE labeled responder cells (FIG. 3b, bottom panel).

We used a T cell transfer model of colitis (Powrie et al., 1993) to test whether Foxp3 induction by TCR signal deprivation and PI3K/mTOR inhibition confers the ability to protect from colitis, which is elicited when naive CD4 T cells are transfered to T cell deficient recipients. (Powrie et al., 1993)

Example 5

Foxp3 Expression in Response to TCR Signal Deprivation and PI3-K/mTOR Inhibition In Vivo We next addressed whether Foxp3 is induced by TCR signal deprivation and PI3-K/mTOR inhibition in vivo. To mimic TCR signal deprivation, we injected activated, CFSE labelled CD62LhiCD4+CD25− LN cells into the tail veins of syngeneic, fully immunocompetent hosts. Two days later we evaluated Foxp3 expression by endogenous (CFSE−) and transfered (CFSE+) CD4 spleen cells (FIG. 4a). With 5.3±4.6% (n=11) the frequency of Foxp3+ cells recovered was 3 times higher than the frequency of Foxp3+ cells contained in the original inocula (1.5±1.1%, summarised in FIG. 4b). When the i.v. transfer of CFSE labeled activated T cells was accompanied by the i.p. injection of rapamycin and Ly294002, the frequency of Foxp3 expressing cells that were recovered 2 days later increased further, to around 10% (FIG. 4). In contrast, the frequency of endogenous (CFSE−) Foxp3+ T cells remained unchanged, excluding the possibility that the inhibitors were selectively toxic to conventional, but not to Foxp3+ CD4 T cells (FIG. 4). We next addressed whether the elevated frequency of Foxp3 expressing cells was due to the selective recovery of Foxp3+ CD4 T cells or to the induction of Foxp3. We transfered CFSE labelled CD62LhiCD4+CD25− LN cells after 48 hours of activation, a time when TCR deprivation no longer efficiently induced Foxp3 expression in vitro (see FIG. 1c). Under these conditions, only 1.3±0.5% of CFSE+ cells expressed Foxp3 after transfer (n=4) and 1.6±0.3% of CFSE+ cells after transfer in the presence of rapamycin and Ly294002 (n=3, FIG. 4b). Hence, TCR signal deprivation predisposes newly activated T cells to Foxp3 expression in synergy with inhibition of the PI3-K/mTOR axis, indicating that PI3-K/mTOR signaling antagonises Foxp3 induction in newly activated T cells in vitro and in vivo.

Example 6

Selective PI3-K Inhibitors Reveal a Hierarchy Among p110 Isoenzymes in the Regulation of Foxp3

A new generation of PI3-K inhibitors has recently been characterised at the biochemical, structural, and biological level and shown to have selectivity for PI3-K isoenzymes in preference over an extensive range of other kinases (Camps et al., Nat Med. 2005, 11:936-943; Knight et al., 2006 ibid.). We utilised these compounds to dissect the role of p110 isoenzymes in the regulation of Foxp3 by titrating them into our T cell differentiation assay. In these experiments, CFSE labeling was used to assess cell cycle progression as a measure of activation and viability, and the induction of Foxp3 was assayed at the single cell level (FIG. 5a, b), along with S6 phosphorylation (FIG. 5b).

p110β and p110γ do not detectably affect Foxp3 expression. TGX115 had a slight impact on Foxp3 expression at 10 μM, where it inhibits both p110β and p110δ. At 0.1 μM, where TGX115 selectively inhibits p110β, it did not affect Foxp3 expression, indicating that p110β plays no significant role in regulating Foxp3 in this setting. Similarly, the p110γ specific inhibitor AS-605240 affected Foxp3 only at concentration far in excess of its IC50 for p110γ (0.008 μM), ruling out a role for p110γ in the regulation of Foxp3 (FIG. 5a, b).

p110α and p110δ regulate Foxp3 expression in newly activated T cells. The inhibitor IC-87114 induced Foxp3 10-15% of cells over and above TCR deprivation alone down to 0.01 μM. At these concentrations, IC-87114 selectively inhibits p110δ, demonstrating a significant contribution of the p110δ isoenzyme to the regulation of Foxp3. The PI-103 compound strongly induced Foxp3, elevating the frequency of Foxp3 expressing cells by >20% above TCR signal deprivation alone. PI-103 induced Foxp3 at concentrations slightly below its in vitro IC50 for mTORC1 (0.02 μM) and around the IC50 for p110α (0.008 μM), consistent with a role for p110α. The p110α specific inhibitor PIK75 could not be used to test this suggestion due to toxicity over the duration of our assay (data not shown). Conclusive evidence came from the analysis of PIK90, which strongly induced Foxp3 at 0.1 μM, where it selectively inhibits p110α and p110γ (FIG. 5a, b). Since our experiments with AS-605240 rule out a role for p110γ, this result identifies p110α as the dominant p110 isoenzyme in the regulation of Foxp3. Based on these studies, the role of p110 isoenzymes in the regulation of Foxp3 appears to be selective: p110β and p110γ play no detectable role, p110δ is moderately important, and p110α is predominant.

Example 7

Involvement of TGFβ in Foxp3 Induction by TCR Signal Deprivation and Inhibition of PI3K/mTOR TGFβ is known as a powerful inducer of Foxp3 expression in conventional CD4 T cells in vitro and we therefore asked whether TGFβ mediates the induction of Foxp3 by TCR signal deprivation of newly activated T cells and PI3-K/mTOR inhibitors. Since cell culture medium supplemented with FCS contains TGFβ, we carried out the experiments described in this section in serum free lymphocyte culture medium (AIM-V, Invitrogen). Real time RT-PCR detected no increase in TGF-β1, the predominant TGFβ isoform in the immune system, but TGF-β regulation is known to be complex and RNA levels do not necessarily correlate with the amount of secreted protein. The binding of TGFβ binding to ALK5 and TGFβ receptor II (TGFβRII) results in the phosphorylation of receptor-associated Smad2 and -3, which subsequently associate with co-Smads, translocate to the nucleus and act as transcriptional regulators. The phosphorylation of Smad proteins therefore provides a sensitive indicator of TGFβ signaling. Naive LN T cells were activated for 18 hours in serum free medium and then exposed to TGFβ (1 ng/ml) for, TCR signal deprivation, or TCR signal deprivation plus rapamycin and Ly294002. Whole cell extracts were subjected to SDS gel electophoresis and western blotting with anti pSmad2 (S465/467) showed strong phosphorylation of Smad2 in response to TGF (FIG. 6a lane 1). In contrast, there was no detectable phosphorylation of Smad2 in response to TCR signal deprivation (FIG. 6a, lane 2), or TCR signal deprivation plus rapamycin and Ly294002 (FIG. 6a, lanes 3 and 4). The blot was subsequently probed with anti Smad2/3 as a loading control.

Next, we sought to inhibit TGFβ signaling using two independent approaches, neutralising antibodies to TGFβ and SB 431542, an inhibitor of TGFβ activin receptor-like kinases (ALKs). SB-431542 is a potent and specific inhibitor of transforming growth factor-beta superfamily type I activin receptor-like kinase (ALK) receptors ALK4, ALK5, and ALK7 (Inman et al 2002 Mol. Pharmacol. vol 62:65-74). Since cell culture medium supplemented with FCS contains TGFβ, we carried out these experiments in serum free lymphocyte culture medium (AIM-V, Invitrogen). Neutralising TGFβ antibodies and SB431542 blocked Foxp3 induction by TGFβ by 85% and 96%, respectively, but had no effect on Foxp3 induction by PI3-K/mTOR inhibitors (FIG. 6b).

TABLE 1

Specificity of the small molecule inhibitors used in FIG. 5 and elsewhere for p100 isoenzymes and other kinases

|  | TGX115 | IC87114 | PIK90 | PI-103 | SA-605240 |
| --- | --- | --- | --- | --- | --- |
| p110α | 61 | >200 | 0.011 | 0.008 | 0.06 |
| p110β | 0.13 | 16 | 0.35 | 0.088 | 0.27 |
| p110δ | 0.63 | 0.13 | 0.058 | 0.048 | 0.3 |
| p110γ | 100 | 61 | 0.018 | 0.15 | 0.008 |
| PI3KC2α | >100 | >100 | 0.047 | ~1 |  |
| PI3KC2β | 50 | >100 | 0.064 | 0.026 |  |

TABLE 1-continued

Specificity of the small molecule inhibitors used in FIG. 5 and elsewhere for p100 isoenzymes and other kinases

|  | TGX115 | IC87114 | PIK90 | PI-103 | SA-605240 |
| --- | --- | --- | --- | --- | --- |
| PI3KC2γ | 100 | >100 | ND | ND |  |
| hsVPS34 | 5.2 | >100 | 0.83 | 2.3 |  |
| PI4Ks |  |  |  |  |  |
| PI4KIIα | >100 | >100 | >100 | >100 |  |
| PI4KIIIα | >100 | >100 | 0.83 | >100 |  |
| PI4KIIIβ | >100 | >100 | 3.1 | ~50 |  |
| PIKKs |  |  |  |  |  |
| ATR | >100 | >100 | 15 | 0.85 |  |
| ATM | 20 | >100 | 0.61 | 0.92 |  |
| DNA-PK | 1.2 | >100 | 0.013 | 0.002 |  |
| mTORC1 | >100 | >100 | 1.05 | 0.02 |  |
| mTORC2 | >100 | >100 | ND | 0.083 |  |
| PIPKs |  |  |  |  |  |
| PI4P5KIα | >100 | >100 | >100 | >100 |  |
| PI4P5KIα | >100 | >100 | >100 | >100 |  |
| PI5P4KIIβ | >100 | >100 | >100 | >100 |  |
| Abl | 121.2 | 103.6 | 103.4 | 100.8 |  |
| Abl (T315I) | 141.2 | 99.4 | 111.3 | 108.1 |  |
| Akt1 | 126.6 | 122.2 | 140.2 | 108.5 | − |
| Akt1 (ΔPH) | 91.4 | 89.6 | 122.4 | 123.1 |  |
| Akt2 | 98.8 | 116.5 | 102.0 | 98.8 |  |
| FAK | 105.5 | 110.1 | 100.0 | 101.8 |  |
| Fyn | 145.7 | 105.3 | 126.1 | 114.2 |  |
| GRK2 | 113.5 | 118.7 | 120.2 | 110.3 |  |
| GSK3β | 114.0 | 104.7 | 85.6 | 105.5 | (+) |
| Hck | 104.9 | 93.0 | 94.7 | 94.9 |  |
| Insulin R. | 108.4 | 115.7 | 102.8 | 106.0 |  |
| JNK1α1 | 99.9 | 88.5 | 94.2 | 83.6 | − |
| JNK2α1 | 104.8 | 107.1 | 90.5 | 81.0 | − |
| JNK2α2 | 95.4 | 87.7 | 83.1 | 76.9 |  |
| IRAK4 | 112.7 | 93.1 | 94.9 | 105.6 |  |
| NEK2 | 125.2 | 114.3 | 103.4 | 120.0 |  |
| PKA | 105.4 | 108.6 | 103.1 | 102.5 | − |
| PKCδ | 103.9 | 104.6 | 100.7 | 101.2 |  |
| PKCε | 108.9 | 114.1 | 105.2 | 103.4 |  |
| PDK1 | 111.2 | 113.4 | 110.4 | 107.5 | − |
| PLK1 | 122.7 | 109.6 | 107.6 | 106.2 |  |
| p38 | 101.2 | 104.1 | 98.5 | 99.8 |  |
| Src | 111.7 | 113.3 | 103.7 | 100.6 | − |
| Src (T338I) | 112.8 | 95.7 | 109.5 | 113.4 |  |
| WNK1 | 107.5 | 109.0 | 108.6 | 104.1 |  |
| Zap70 | 123.8 | 110.5 | 115.8 | 117.7 | − |
| Akt2 (ΔPH) | 104.4 | 117.8 | 108.5 | 112.6 |  |
| Akt3 | 97.6 | 111.0 | 113.3 | 103.5 |  |
| CamKII | 111.4 | 115.4 | 116.1 | 127.6 | − |
| CDK1/cyc.B | 103.0 | 116.0 | 126.6 | 142.3 | (+) |
| CDK2/cyc.A | 105.3 | 102.4 | 100.9 | 98.5 | − |
| Chk1 | 119.9 | 103.0 | 102.9 | 92.3 | − |
| CK1 | 99.7 | 98.1 | 97.8 | 84.8 | (+) |
| CK2 | 103.3 | 111.7 | 103.1 | 108.1 |  |
| Erk1 | 96.7 | 93.7 | 98.8 | 92.0 |  |
| Erk2 | 107.7 | 104.7 | 119.8 | 114.7 |  |

Summary of Examples 1-7

We show that TCR signaling and PI3-K/mTOR activity antagonises the induction of Foxp3 in newly activated T cells. Without wishing to be bound by theory, this finding has important implications for understanding immune regulation, as it links the choice between effector and regulatory T cell fate to the termination of TCR signaling. Effective immune responses reduce antigen load and create conditions where the availability of antigen becomes limiting. Our results indicate how immune regulation may be linked to the involution phase of immune responses, which is important for T cell homeostasis and for limiting immune pathology.

Pharmacological inhibition of the PI3K/mTOR axis potentiates Foxp3 induction triggered by deprivation of TCR signals. The involvement of PI3K/mTOR is selective, since blockade PKC, N-FAT, GSK-3, MAPK, Notch and others does not results in Foxp3 induction in the systems of the examples. PI3-K activity persists for many hours following T cell activation and our findings demonstrate that the PI3K/mTOR axis is critical in preventing the induction of Foxp3 in newly activated T cells. The class I PI3-kinases are subdivided into two groups, A and B, based on the selective involvement of p110 isoezymes, the catalytic subunits of PI3-K. The expression of p110δ and p110γ subunits is mainly resticted to leukocytes, whereas p110α and p110β are ubiquitously expressed and essential for embryonic development. p110γ, the single member of Class IB, is important for T cell development and activation and a major target for the treatment of inflammatory responses and autoimmune disease. The link between PI3K signaling and disease has provided a major driver for the development and introduction into the clinic of selective inhibitors of PI3-K subunits. We have employed extensively characterised selective inhibitors to show selectivity among p110 isoenzymes where p110α and p110δ, but not p110β or p110γ regulate Foxp3. While p110γ is activated by G-protein-coupled receptors, the class IA PI3Ks p110α, p110δ and p110β are typically activated downstream of receptor tyrosine kinases and therefore involved in lymphocyte receptor signalling. Interestingly, the hierarchy among IA PI3 Ks in Foxp3 regulation appears to be distinct from their relative contribution to TCR stimulated PI3-K activity. Genetic and pharmacological analysis both point to a prominent role for p110δ in antigen receptor signaling in B and in T lymphocytes, while our data show that p110δ has a significant, but less dominant role in Foxp3 regulation, where p110α appears to dominate. The functional distinction between p110 isoforms in TCR signaling and Foxp3 regulation assists the skilled worker in manipulation of the immune response.

p110δ deficient mice not only show defects in lymphocyte activation, they also develop inflammatory bowel disease, the hallmark of Treg deficiency. A potential explanation for this is suggested by the dependence of Treg tolerance on mast cell-derived IL-9 and the essential role of p110δ for mast cell function. Consistent with these data, Treg function is impaired in the periphery of p110δ deficient mice. This notwithstanding, the differentiation of Tregs is increased in the p110δ deficient thymus in agreement with our findings.

Both PI3-K inhibitors and rapamycin have been used to repress unwanted immune responses but the mechanisms by which PI3-K/mTOR inhibitors regulate immunity are largely unknown. A link between PI3-K inhibitors and autoimmunity was suggested by the finding that mice heterozygous for Pten, an antagonist of PI3-K signaling, developed autoimmunity as well as other observations. PI3-Ks regulate numerous processes in multiple cell types and potential mechanisms for the involvement of PI3-Ks in autoimmunity include the increased survival of T cells and the recruitment and activation of antigen presenting cells, mast cells and other inflammatory cell types. Rapamycin had previously been reported to affect regulatory T cell numbers positively or negatively in long term assays. Our findings establish the regulation of Foxp3 as a mechanism by which PI3-K/mTOR inhibitors modulate immunity.

In contrast to the class IA isoenzymes p110α and δ, the class IB PI3-K isoenzyme p110γ functions predominantly downstream of G protein-coupled receptors (rather than src tyrosine kinases), and PI3-Kγ does not significantly regulate Foxp3. Nevertheless, PI3-Kγ plays an important role in T cell development and activation and has recently been recognised as a target for the treatment of autoimmune disease. Inhibitors of PI3-Kγ are effective drugs in the prevention and in the treatment of autoimmunity, but—as we demonstrate—not via the induction of Foxp3 in newly activated T cells.

Earlier studies had linked rapamycin to deletion or the protracted expansion of pre-existing Tregs, especially in combination with growth factor withdrawal, but rapamycin appeared to have no effect on the de novo induction of Foxp3. Here we show rapid de novo induction of Foxp3 by rapamycin in combination with TCR signal deprivation.

TGFβ is a potent inducer of Foxp3 in naive CD4 T cells and we therefore asked whether TGFβ is involved in the induction of Foxp3 by TCR signal deprivation of newly activated T cells and PI3-K/mTOR inhibitors. We found no evidence that newly activated T cells increase TGFβ production in response to TCR signal deprivation and inhibition of PI3K/mTOR. Foxp3 induction was efficient in serum free medium, which excludes a requirement for serum-derived TGFβ. Our findings show that TCR signal deprivation and PI3-K/mTOR inhibitors do not result in detectable phosphorylation of Smad2 and that Foxp3 induction by TCR signal deprivation and PI3-K/mTOR inhibitors is independent of exogenous TGFβ resistant to neutralising anti-TGFβ and resistant to SB431542. They are therefore consistent with a model in which PI3-K/mTOR inhibitors induce Foxp3 by a pathway independently of TGFβ.

In summary, we have identified a novel, TGFβ independent pathway of Foxp3 induction in newly activated naive T cells. Our findings highlight the importance of TCR signaling for the choice between effector fate and Treg function and we describe new approaches to drive regulatory T cell differentiation by small molecule inhibitors of PI3K/mTOR signaling in situations where the manipulation of immune responses is desirable.

Example 8

Induction of De Novo Foxp3 Expression

We teach that activation of naive CD4 T cells creates a window of opportunity for the induction of Foxp3 expression, controlled by PI3K/mTOR signaling.

Overview: Activation reveals the potential of naive CD4 T cells to differentiate towards a range of T helper (Th) cell types, or, alternatively, to adopt a regulatory T cell (Treg cell) fate. How the effector versus regulatory cell fate choice is controlled is largely unknown in the prior art. We show that expression of the Treg cell signature transcription factor Foxp3 is induced when naive CD4 T cells are deprived of TCR signals soon after activation. Foxp3 induction is controlled by phosphatidyl inositol 3 kinase (PI3K) catalytic subunits p110α and p110δ, Akt and mTOR. These findings link TCR signal transduction pathways to the choice of Treg cell fate. The invention provides new approaches for the experimental and therapeutic manipulation of regulatory T cell differentiation.

Introduction: Specialised cell types in multicellular organisms are defined by specific patterns of gene expression. During their differentiation from multipotent hematopoietic stem cells, developing T cells undergo considerable restriction of their lineage potential. Options that remain open to naive CD4 T cells include several distinct Th subsets (such as Th1, Th2 and Th17) and the Treg cell fate. The choice of Th lineage is important for effective immune responses to specific pathogens, while the balance between effector and regulatory functions is critical to ensure immune competence while avoiding excessive immune pathylogy and autoimmunity. Natural regulatory T cells are characterised by the expression of the signature transcription factor Foxp3 and stable high level expression of Foxp3 is both necessary and sufficient for regulatory T cell function. Treg cells arise in the thymus and from naive peripheral CD4 T cells. TGFβ instructs Foxp3 expression in vitro but, like IL-2, is important for the maintenance of Treg cells in vivo rather than for Treg cell differentiation. Since the molecular basis of the choice between effector and regulatory T cell fate is unknown in the prior art, we set out to identify signals that induce Foxp3 expression and regulatory T cell function in naive CD4 T cells.

Experimental: Naive $CD4^+CD25^-$ cells are activated with plate bound anti-TCR and soluble anti-CD28 for 18 hours and then moved to fresh wells with soluble anti-CD28 only. Two days later, real time RT-PCR showed elevated expression of Foxp3 RNA in cells deprived of TCR signals compared to controls exposed to continuous TCR signals (FIG. 7a) and Foxp3 protein was detected 10.8±7.6% (n=30) of cells deprived of TCR signals, but only in 1.0±0.8% (n=21) of cells left in contact with TCR antibody (FIG. 7b). To identify pathways that control Foxp3 downstream of TCR signaling we screened small molecule inhibitors of enzymes involved in signal transduction Inhibitors of PI3K and mTOR markedly potentiated Foxp3 induction (FIG. 7b), whereas inhibitiors of calcineurin/NFAT (cyclosporin A and FK-506), mitogen activated kinases (MAPKs JNK, SAPK, p38 and upstream kinases), protein kinase-C isoenzymes, glycogen synthase kinase-3, hypoxia inducible factor, and γ-secretase/Notch did not. The mTOR inhibitor rapamycin induced Foxp3 in 26.8±14.4% of cells (n=30, FIG. 7b). Similarly, the PI3K inhibitors LY294002 and Wortmannin induced Foxp3 in 26.9±11.4% (n=25, FIG. 7b) and 17.3±5.3% of cells, respectively (n=3,). The LY294002 derivative LY303511 does not inhibit PI3K due to a single atom substitution in the morpholine ring and did not induce Foxp3 expression. TGFβ was used as a positive control (FIG. 7b). To address whether increased Foxp3 expression resulted from the selective expansion of pre-existing $Foxp3^+$ cells, we labelled naive CD4 T cells with CFSE prior to activation. No cell division had occurred after 18 hours, when the cells were exposed to inhibitors. Rapamycin and LY294002 slightly reduced the number of cell divisions that occurred during the next 24-48 hours, yet substantially enhanced the frequency of Foxp3 expression (FIG. 7b) and Foxp3 was expressed in many cells that had not undergone cell division (FIG. 7b). Hence, TCR signal deprivation and PI3K/mTOR inhibitors induce Foxp3 expression in naive CD4 T cells.

T cell activation was required for Foxp3 induction (FIG. 7c) and costimulation markedly enhanced its efficiency.

Costimulation markedly enhanced the efficiency of Foxp3 induction in response to TCR signal deprivation and PI3K/mTOR inhibition:

|  | TCR signal depriv. | rapamycin | LY294002 |
|---|---|---|---|
| anti-TCR | 3% $Foxp3^+$ | 10% $Foxp3^+$ | 4% $Foxp3^+$ |
| anti-TCR + anti-CD28 | 9% $Foxp3^+$ | 25% $Foxp3^+$ | 44% $Foxp3^+$ |

To explore the temporal relationship between T cell activation and Foxp3 induction, we withdrew TCR stimulation and inhibited PI3K/mTOR at different times (FIG. 7c). Foxp3 induction was maximal when T cells were activated for 18 hours prior to PI3K/mTor inhibition. Earlier addition of inhibitors blocked cell division and resulted in less efficient induction of Foxp3. Similarly, Foxp3 induction was inefficient when at later time points, once cell division had occurred (FIG. 7c). We conclude that T cell activation creates a window of opportunity for Foxp3 induction.

Once induced, Foxp3 expression was mitotically heritable and maintained through several rounds of restimulation (FIG. 7d). Foxp3 expression was accompanied by regulatory T cell function, since Foxp3-induced cells (36% $Foxp3^+$) efficiently blocked cell division of CFSE labelled CD4 LN T cells in response to soluble anti CD3 (FIG. 7e, top panel), while control activated cells (1% $Foxp3^+$) did not (FIG. 7e, bottom panel). Resting or control activated $CD45RB^{hi}$ CD4 T cells cause colitis when transfered to lymphocyte deficient ($Rag^{-/-}$) mice whereas colitis was markedly less severe when Foxp3 had been induced in a proportion of $CD45RB^{hi}$ CD4 T cells (28% $Foxp3^+$) prior to transfer (FIG. 7f).

While peripheral CD4 T cells can give rise to 'adaptive' Treg cells, their physiological relevance compared to Treg cells that arise 'naturally' in the thymus is an area of interest. To address whether manipulations of TCR signal transduction drive Foxp3 expression in thymocytes, we activated CD4 single positive, CD25 negative thymocytes for 18 hours and added PI3K/mTOR inhibitors (FIG. 7f). Analysis of Foxp3 expression 2 days later demonstrated the induction of Foxp3 in a sizeable fraction of thymocytes.

A new generation of PI3K inhibitors have recently been characterised at the biochemical, structural, and biological level. Selectivity of these compounds for PI3K isoenzymes has been extensively validated by in vitro kinase assays and cell-based experiments (see Table 1) and by directly comparing the effects of pharmacological and genetic ablation on insulin signaling and lymphocyte activation. We utilised these compounds to define the involvement of PI3K catalytic subunits in the control of Foxp3. The TGX115 compound had a slight impact on Foxp3 expression at 10 μM, where it inhibits both p110β and p110δ but did not affect Foxp3 expression at 0.1 μM, where it selectively inhibits p110β. Similarly, the p110γ-specific inhibitor AS-605240 affected Foxp3 only at concentrations far in excess of its $IC_{50}$ for p110γ (0.008 μM, indicating that p110β and p110γ play no significant role in regulating Foxp3 in this setting (FIG. 8a, b). The IC-87114 compound consistently induced Foxp3 in 10-15% of cells over and above TCR deprivation alone at concentrations where it selectively inhibits p110δ (0.01 μM), demonstrating a significant contribution of p110δ to the regulation of Foxp3. The PI-103 compound strongly induced Foxp3, elevating the frequency of Foxp3 expressing cells by >20%. PI-103 induced Foxp3 at concentrations slightly below its in vitro $IC_{50}$ for mTOR (0.02 μM) and around the in vitro $IC_{50}$ for p110α (0.008 μM), consistent with a role for p110α. The p110α-specific inhibitor PIK75 could not be used to test this suggestion due to toxicity over the duration of the assay. Conclusive evidence for a role of p110α came from the analysis of PIK90, which strongly induced Foxp3 at 0.1 μM, where it selectively inhibits p110α and p110γ (FIG. 8a, b). Since p110γ inhibition did not affect Foxp3 induction (see above) this result identifies p110α as the dominant p110 isoenzyme in this setting. This hierarchy of p110 isoenzymes (α>δ>>>β and γ) appears to set Foxp3 regulation apart from lymphocyte activation, where p110δ is considered as dominant.

Of course in vitro IC50 values must be treated as guidance for cellular IC50s; cellular values are typically somewhat higher because of competition from ATP. IC87114 is extremely p110δ selective, esp. at 1 μM, so the 15% induction at that concentration is clearly due to δ. TGX-115 has very little effect even at 10 μM (where minor δ inhibition is obtained), so beta is likely of limited or peripheral importance. The α inhibitors 103 and 90 show dramatic induction above IC87114 at low doses, showing that α plays a significant role. The window between α and δ for those compounds is not very large though, so the key observation is that they have more activity than IC87114 does at fully δ inactivating doses (10 μM). The interpretation of the AS-605240 data depends on what the cellular IC50 for that compound is for γ; at 10 μM some α inhibition is obtained with this compound. Thus it is very unlikely that gamma would be coupled to TCR signaling in this context.

TGFβ is a powerful inducer of Foxp3 expression in conventional CD4 T cells in vitro and we addressed its role in our system. The binding of TGFβ binding to ALK5 and TGFβ receptor II (TGFβRII) results in the phosphorylation of receptor-associated Smad2 and -3, which provides a sensitive indicator of TGFβ signaling. pSmad2 (S465/467) was readily detectable in response to TGFβ (FIG. 9a lane 1) but not in response to TCR signal deprivation (FIG. 9a, lane 2), or PI3K/mTOR inhibition (FIG. 9a, lanes 3 and 4). Neutralising TGFβ antibodies and SB 431542, which blocks TGFβ activin receptor-like kinases, reduced Foxp3 induction by TGFβ (by 85% and 96%, respectively), but had no effect on Foxp3 induction by PI3K/mTOR inhibitors (FIG. 9b), demonstrating that TGFβ is dispensable for the induction of Foxp3 by TCR signal deprivation and PI3K/mTOR inhibition.

To monitor the activity of the PI3K/mTOR axis in newly activated CD4 T cells we analysed phosphorylation of S6 ribosomal protein (pS6), a target of the mTOR-regulated p70 S6 kinase S6K1. TCR/CD28 signaling (but not anti-CD28 alone) induced high levels of pS6 (FIG. 10a). The maintenance of mTOR activity in 18 hour activated T cells required continued TCR signaling, since S6 phosphorylation declined when TCR signals were withdrawn (FIG. 10b). S6 phosphorylation was completely removed by rapamycin or LY294002 (FIG. 10b). The serine/threonine protein kinase Akt/PKB is rapidly phosphorylated in response to signaling through TCR/CD28 but, in contrast to pS6, pAkt (S473) was no longer detected 18 h after initiation of TCR/CD28 signaling (FIG. 10c). Akt (S473) phosphorylation was restored, however, when 18 h activated T cells were deprived of TCR signals, which resulted in increasing levels of pAkt at 1, 3, and 8 hours and a reciprocal decline in pS6 levels (FIG. 10c). Exposure to rapamycin for 1 hour had a similar effect. Increased Akt phosphorylation in response to TCR signal deprivation and rapamycin treatment is incompatible with a traditional linear signaling pathway (FIG. 10d) but consistent with a network model in which Akt activity is controlled both by PDK1 and by mTORC2. In this model, mTORC2 (mTOR/rictor/Sin 1) is under negative feedback control of mTORC1 (mTOR/raptor) via S6K1, which phosphorylates and inhibits IRS1 (insulin receptor substrate 1) and reduces Akt activation via PI3K, PDK1 and mTORC2 (FIG. 10e). Applied to our data, withdrawal of TCR signaling lowers mTORC1 and S6K1 activity (FIG. 10b), which reduces feedback inhibition of mTORC2 and explains the observed increase in pAkt (S473) (FIG. 10c). Similarly, short-term treatment with rapamycin blocks mTORC1-dependent feedback inhibition of mTORC2, resulting in Akt (S473) phosphorylation (FIG. 10c, e). Interestingly, TGFβ also results in reduced pS6 and increased pAkt S473, and in this regard mimics TCR signal deprivation and mTOR inhibition (FIG. 10c).

Reduced S6 phosphorylation alone was not sufficient to induce Foxp3 expression, since nutrient deprivation of 18 hour activated CD4 T cells inhibited pS6 but did not induce Foxp3 (continued TCR signaling: 2% Foxp3$^+$; TCR signal deprivation 11% Foxp3$^+$; rapamycin: 25% Foxp3$^+$; IMDM culture medium with 0.1% FCS: 4% Foxp3$^+$; PBS with 10% FCS: 5% Foxp3$^+$; PBS with 0.1% FCS: 2% Foxp3$^+$). It remains open whether the induction of Foxp3 by TCR signal deprivation is due to increased Akt activity following the loss of mTORC1-mediated feedback inhibition, or, alternatively, to the eventual loss of Akt activity, which occurs when long term exposure to rapamycin interferes with the assembly of mTORC2, and consequently with the phosphorylation of Akt (S473). To address this question, we used an allosteric inhibitor, Akti-1/2. Akti-1/2 enhanced Foxp3 expression in recently activated T cells at concentrations around its IC50 for Akt1 and Akt2 (58 nM and 210 nM, respectively), demonstrating that Akt inhibition, not Akt activation drives Foxp3 induction (FIG. 10f).

SUMMARY

In summary, we have shown that activation creates a window of opportunity for the induction of Foxp3 in naive CD4 T cells. Foxp3 induction appears independent of TGFβ and is antagonised by PI3K/mTOR/Akt signaling. This finding has important implications for understanding immune regulation, as it links the choice between effector and regulatory T cell fate to TCR signal transduction pathways. Consistent with our finding that p110δ regulates Foxp3 expression, higher than normal numbers of Treg cells are generated in the thymi of p110δ deficient mice. In the longer term, p110δ deficiency impairs Treg cell maintenance and function, possibly because p110δ is important for other cell types such mast cells, which in turn affect Treg cells. These considerations, together with the differential role of p110 isoenzymes in Foxp3 regulation we have demonstrated enable new strategies for manipulating the immune response. A potential obstacle to the generation of antigen specific Treg cells by PI3K/mTOR inhibition is if the approach requires the removal of TCR ligands to allow Foxp3 induction. However, we show that PI3K/mTOR inhibitors induce Foxp3 in a sizeable proportion of naive CD4 T cells in the continued presence of anti CD3/CD28 beads (FIG. 12). Foxp3 was also inducible by PI3K/mTOR inhibition in Rag1 deficient AND TCR transgenic CD4 LN cells stimulated by antigen presenting cells and specific peptide, demonstrating that it is advantageously now possible to generate antigen specific Treg cells using PI3K/mTOR inhibitors.

Interestingly, compromised PI3K/mTOR/Akt signaling not only favours Treg cell differentiation, but Akt signaling is reportedly compromised in Treg cells and their targets, raising the possibility that regulatory T cell function involves alterations in PI3K/mTOR/Akt signaling.

Lack of sustained TCR engagement or compromised TCR signaling may occur in situations relevant to immune regulation, such as antigen presentation by non-professional APCs, low antigen dose during the involution phase of immune responses or mosaic antigen expression. This is consistent with the selection of Treg cells by epithelial cells ectopically expressing tissue-specific antigens in the thymus and in lymph nodes.

Materials and Methods for Example 8

Mice, Cell Sorting and Culture. Animal work was carried out according to the Animals (Scientific Procedures) Act, UK. Lymph node (LN) cells or thymocytes from wild type were stained, analysed and sorted by flow cytometry as described (Thompson et al., 2007 Immunity Vol 26 pp 335-344) from wild type (C57BL/6, BALB/c or C57BL/6×129) mice or from Rag1 deficient H2$^b$ AND TCR transgenic mice. Antigen presenting cells were derived from bone marrow in the presence of GM-CSF and incubated with antigenic peptide. Intracellular staining for Foxp3 protein was done as advised by the manufacturers (eBiosciences.com). The phosphorylation status of S6 ribosomal protein was determined using anti pS6 Ser235/236 (Cell Signaling cat.no. 2211, http://www.cellsignal.com) using the eBioscience Foxp3 staining kit and anti rabbit IgG-FITC or IgG-Cy5 (Jackson ImmunoResearch). For induction of Foxp3 expression, sorted LN CD4$^+$CD25$^-$CD62L$^{bi}$ T cells were cultured at 1-3×10$^6$/ml with plate bound anti-TCRβ (H57, Pharmingen, 200 ng/ml) and soluble or plate-bound anti-CD28 (2 μg/ml, Pharmingen). After 18 hours the cells were either left in place for continued TCR stimulation or moved to uncoated wells with the indicated additives. To assess regulatory function, CD4 T cells cultured as indicated were titrated into round bottom wells containing either 1×10$^5$ CFSE labeled total LN cells or 5×10$^4$ CFSE labeled CD4$^+$CD25$^-$ T cells and 1×10$^5$ mitomycin-C treated (25 μg/ml, 20 min, 37° C.) T cell depleted splenocytes with the indicated concentrations of anti CD3 (2C11, Pharmingen). CD4 T cell CFSE profiles were recorded between 48 and 72 hours later.

Adoptive Transfer Experiments. CD4$^+$ CD25$^-$ CD45RB$^{hi}$ naive CD4 cells were transfered into lymphocyte deficient (Rag$^{-/-}$) hosts and colitis was scored as described (Powrie et al., 1993 Int. Immunol. Vol 5 pp 1461-1471).

RT-PCR and Northerns and Immunoblots. Total RNA was isolated using RNAbee (Tel-Test, Friendswood, Tex.) and reverse transcribed. Real-time PCR analysis was carried out on an Opticon™DNA engine (MJ Research Inc.; 95° C. for 15 min followed by 40 cycles of 94° C. for 15 s, 60° C. for 30 s and 72° C. for 30 s with a plate read at 72° C.) and normalised to the geometric mean of Ywhaz (tyrosine 3-monooxygenase/tryptophan 5-monooxygenase activation protein, zeta polypeptide) and Ube2L3 (ubiquitin conjugating enzyme E2L3) as described (Thompson et al., 2007 above). Primer sequences (5' to 3')

```
Ywhaz forward:
                                  (SEQ ID NO. 1)
CGTTGTAGGAGCCCGTAGGTCAT Ywhaz reverse:
                                  (SEQ ID NO. 2)
TCTGGTTGCGAAGCATTGGG Ubc forward:
                                  (SEQ ID NO. 3)
AGGAGGCTGATGAAGGAGCTTGA Ubc reverse:
                                  (SEQ ID NO. 4)
TGGTTTGAATGGATACTCTGCTGGA Foxp3 forward:
                                  (SEQ ID NO. 5)
ACTCGCATGTTCGCCTACTTCAG Foxp3 reverse:
                                  (SEQ ID NO. 6)
GGCGGATGGCATTCTTCCAGGT
```

Immunoblots were done as described (Thompson et al., 2007 above).

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method for generating a regulatory T-cell from a naïve T cell, comprising
   (i) stimulating the naïve T cell with a T cell receptor (TCR) stimulant;
   (ii) removing the TCR stimulant;
   (iii) contacting the stimulated naïve T cell with an exogenous inhibitor of PI3K alpha, PI3K delta, m-TOR, or Akt, wherein said contacting is commenced 10 to 22 hours after the stimulation of (i), and after the removal of the TCR stimulant.

2. A method for generating a regulatory T-cell comprising treating a stimulated CD8− T cell with phosphatidyl inositol 3 kinase (PI3K) inhibitor wherein said inhibitor inhibits PI3K alpha and/or PI3K delta.

3. A method of inducing de novo Foxp3 expression in a naïve T cell comprising:
   (i) stimulating the naïve T cell;
   (ii) halting the stimulating of (i) after about 10 to 22 hours of stimulation;
   (iii) contacting the stimulated naïve T cell with an exogenous inhibitor of PI3K alpha, PI3K delta, m-TOR, or Akt, wherein the contacting is commenced 10 to 22 hours after the stimulation of (i), and after the halting of (ii); and
   (iv) determining that Foxp3 expression has been induced in said cells wherein said T cells do not comprise or have been depleted of CD8+ T cells and are CD4+.

4. A method of inducing de novo Foxp3 expression in a naïve T cell comprising:
   (i) stimulating the naïve T cell with a T cell receptor (TCR) stimulant for about 10 to 22 hours;
   (ii) contacting the stimulated naïve T cell with an exogenous inhibitor of PI3K alpha, PI3K delta, m-TOR, or Akt, wherein the contacting is commenced 10 to 22 hours after the stimulation of (i); and
   (iii) determining that Foxp3 expression has been induced in said cells wherein said T cells do not comprise or have been depleted of CD8+ T cells and are CD4+.

5. A method of inducing Foxp3 expression in a previously stimulated naïve T cell which does not express Foxp3, comprising contacting said previously stimulated naïve T cell with an inhibitor of PI3K alpha, PI3K delta, m-TOR, or Akt, wherein said contacting is commenced 10 to 22 hours after the stimulation, and wherein determining that Foxp3 expression has been induced in said contacted T cells and wherein said T cells to not comprise or have been depleted of CD8+ T cells and are CD4+.

6. A method of treating a subject in need of regulatory T cell(s) comprising
   (i) removing a sample comprising a T cell from a subject
   (ii) stimulating said T cell
   (iii) optionally withdrawing said stimulation
   (iv) inhibiting signalling via PI3K alpha or PI3K delta or m-TOR or Akt in said T cell, wherein said inhibition is commenced 10 to 22 hours after the stimulation of (i); and
   (v) reintroducing said T cell to said subject.

7. The method according to claim 4 wherein said inhibition is commenced about 17 to 19 hours after the stimulation.

8. The method according to claim 7 wherein said inhibition is commenced about 18 hours after the stimulation.

9. The method according to claim 4 wherein the inhibiting signalling step comprises inhibiting signalling via PI3K alpha or PI3K delta.

10. The method according to claim 9 wherein inhibiting signalling via PI3K alpha or PI3K delta comprises contacting said cell with PI3K inhibitor, and wherein said inhibitor inhibits PI3K alpha and/or PI3K delta.

11. The method according to claim 4 further comprising withdrawing said stimulation no later than at the time of inhibiting signalling.

12. The method according to claim 4 wherein stimulating said T cell comprises stimulating said T cell via the T cell receptor (TCR).

13. A method of inducing differentiation of a naïve T cell into a regulatory T cell comprising contacting said naïve T cell with a PI3K inhibitor wherein said inhibitor inhibits PI3K alpha and/or PI3K delta.

14. The method according to claim 9 wherein said PI3K alpha and/or PI3K delta inhibitor comprises LY294002.

15. A kit comprising
   (i) a TCR stimulant; and
   (ii) an inhibitor of PI3K alpha or delta.

16. The kit according to claim 15 wherein said TCR stimulant comprises anti-TCR and anti-CD28 antibody.

17. The kit according to claim 15 further comprising an m-TOR inhibitor.

18. The kit according to claim 17 wherein said m-TOR inhibitor is rapamycin.

19. The kit according to claim 15 further comprising an Akt inhibitor.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
cgttgtagga gcccgtaggt cat                                           23

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tctggttgcg aagcattggg                                               20

<210> SEQ ID NO 3
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 3
aggaggctga tgaaggagct tga                                              23

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
tggtttgaat ggatactctg ctgga                                            25

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
actcgcatgt tcgcctactt cag                                              23

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
ggcggatggc attcttccag gt                                               22
```